US010639371B2

(12) United States Patent
Kiick et al.

(10) Patent No.: US 10,639,371 B2
(45) Date of Patent: May 5, 2020

(54) THERMORESPONSIVE BIOCONJUGATES AND THEIR CONTROLLED DELIVERY OF CARGO

(71) Applicants: Kristi Kiick, Rising Sun, MD (US); Tianzhi Luo, Newark, DE (US)

(72) Inventors: Kristi Kiick, Rising Sun, MD (US); Tianzhi Luo, Newark, DE (US)

(73) Assignee: University of Delaware, Newark, DE (US)

(*) Notice: Subject to any disclaimer, the term of this patent is extended or adjusted under 35 U.S.C. 154(b) by 20 days.

(21) Appl. No.: 15/747,552

(22) PCT Filed: Jul. 29, 2016

(86) PCT No.: PCT/US2016/044917
§ 371 (c)(1),
(2) Date: Jan. 25, 2018

(87) PCT Pub. No.: WO2017/020025
PCT Pub. Date: Feb. 2, 2017

(65) Prior Publication Data
US 2018/0236074 A1    Aug. 23, 2018

Related U.S. Application Data

(60) Provisional application No. 62/198,193, filed on Jul. 29, 2015, provisional application No. 62/315,079, filed on Mar. 30, 2016.

(51) Int. Cl.
| | | |
|---|---|---|
| *A61K 38/00* | (2006.01) | |
| *A61K 41/00* | (2020.01) | |
| *C07K 14/78* | (2006.01) | |
| *A61K 47/69* | (2017.01) | |
| *A61K 47/62* | (2017.01) | |
| *A61P 19/02* | (2006.01) | |
| *A61P 35/00* | (2006.01) | |
| *A61K 38/39* | (2006.01) | |

(52) U.S. Cl.
CPC .......... *A61K 41/0028* (2013.01); *A61K 38/39* (2013.01); *A61K 47/62* (2017.08); *A61K 47/6907* (2017.08); *A61K 47/6931* (2017.08); *A61K 47/6935* (2017.08); *A61P 19/02* (2018.01); *A61P 35/00* (2018.01); *C07K 14/78* (2013.01); *A61K 38/00* (2013.01)

(58) Field of Classification Search
None
See application file for complete search history.

(56) References Cited

U.S. PATENT DOCUMENTS

2007/0099244 A1 * 5/2007 Xu ........................ C07K 14/78
                                                                 435/7.2
2007/0161081 A1    7/2007 Jin et al.
2007/0265197 A1   11/2007 Furgeson et al.
2009/0203627 A1    8/2009 Hook et al.
2011/0039776 A1 * 2/2011 Chilkoti ............. A61K 38/1709
                                                                 514/11.7
2013/0164220 A1    6/2013 Yu et al.

FOREIGN PATENT DOCUMENTS

JP         2015-013850 A        1/2015

OTHER PUBLICATIONS

Sun, Journal of Controlled Release 155 (2011) 218-226. (Year: 2011).*
Walker, International Journal of Pharmaceutics 436 (2012) 825-832 (Year: 2012).*
International Preliminary Report on Patentability and Written Opinion for International Application No. PCT/US2016/044917, dated Jan. 30, 2018, 9 pages.
International Search Report for PCT Application No. PCT/US2016/044917 dated Dec. 28, 2016.
Fukushima et al., Colloids and Surfaces B: Biointerfaces, 132:155-60 (2015).
Hathorne et al., Biotechnology and Bioengineering, 110(7):1822-30 (2013).
Janib et al., Polym. Chem., 5:1614-25 (2014).
Nuhn et al., Biomacromolecules, 9:2755-63 (2008).
Koga et al., Macromol. Biosci., 12:1043-47 (2012).
Lemieux et al., Chem. Commun., 46:3071-73 (2010).
Navon et al., Biomacromolecules, 17:262-70 (2016).
Pechar et al., Macromol. Biosci., 7:56-69 (2007).
Reiersen et al., J. Mol. Biol., 283:255-64 (1998).
Taniguchi et al., J .Pept Sci., 22:36-42 (2016).
van Eldijk et al., J. Am. Chem. Soc., 134:18506-09 (2012).
Ayres et al., Macromolecules, 36:5968-73 (2003).
Domeradzka et al., Current Opinion in Biotechnology, 39:61-67 (2016).
Kobayashi et al., J. Am. Chem. Soc., 137:11285-93 (2015).
Kojima et al., Biopolymers, 100(6):714-21 (abstract only) (2013).
Maeda et al., Protein and Peptide Letters, 22(10):934-39 (abstract only) (2015).
Maeda et al., Protein & Peptide Letters, 20(8):905-10 (abstract only) (2013).

* cited by examiner

*Primary Examiner* — Satyanarayana R Gudibande
(74) *Attorney, Agent, or Firm* — RatnerPrestia

(57) ABSTRACT

The present invention provides a bioconjugate. The bioconjugate comprises a first molecule comprising an elastin-like peptide (ELP), a second molecule capable of self-associating into an oligomer, and a linker connecting the first molecule with the second molecule. The bioconjugate is self-assembled into particles, which are disassembled when the temperature is increased. Also provided is a method for delivering a bioconjugate to a target matrix, comprising (a) introducing a bioconjugate self-assembled into particles to a target matrix, wherein the bioconjugate comprises a first molecule comprising an elastin-like peptide (ELP), a second molecule capable of self-associating into an oligomer, and a linker connecting the first molecule with the second molecule, and (b) increasing the temperature of the target matrix to disassemble the particles at the target matrix.

20 Claims, 12 Drawing Sheets
Specification includes a Sequence Listing.

A.

B.

A.

B.

A.

B.

SEQUENCE LISTING

```
<160> NUMBER OF SEQ ID NOS: 31

<210> SEQ ID NO 1
<211> LENGTH: 37
<212> TYPE: PRT
<213> ORGANISM: Artificial Sequence
<220> FEATURE:
<223> OTHER INFORMATION: Synthetic

<400> SEQUENCE: 1

Ala Ser Ile Ala Arg Leu Glu Glu Lys Val Lys Thr Leu Lys Ala Gln
1               5                   10                  15

Asn Tyr Glu Leu Ala Ser Thr Ala Asn Met Leu Arg Glu Gln Val Ala
            20                  25                  30

Gln Leu Gly Ala Pro
        35

<210> SEQ ID NO 2
<211> LENGTH: 37
<212> TYPE: PRT
<213> ORGANISM: Artificial Sequence
<220> FEATURE:
<223> OTHER INFORMATION: Synthetic

<400> SEQUENCE: 2

Ala Ser Thr Asp Thr Leu Gln Ala Glu Thr Asp Gln Leu Glu Asp Glu
1               5                   10                  15

Lys Tyr Ala Leu Gln Thr Glu Ile Ala Asn Leu Leu Lys Glu Lys Glu
            20                  25                  30

Lys Leu Gly Ala Pro
        35

<210> SEQ ID NO 3
<211> LENGTH: 46
<212> TYPE: PRT
<213> ORGANISM: Artificial Sequence
<220> FEATURE:
<223> OTHER INFORMATION: Synthetic
```

<400> SEQUENCE: 3

Gly Asp Phe Asn Arg Gln Phe Leu Gly Gln Met Thr Gln Leu Asn Gln
1               5                   10                  15

Leu Leu Gly Glu Val Lys Asp Leu Leu Arg Gln Gln Val Lys Glu Thr
                20                  25                  30

Ser Phe Leu Arg Asn Thr Ile Ala Glu Cys Gln Ala Cys Gly
            35                  40                  45

<210> SEQ ID NO 4
<211> LENGTH: 46
<212> TYPE: PRT
<213> ORGANISM: Artificial Sequence
<220> FEATURE:
<223> OTHER INFORMATION: Synthetic

<400> SEQUENCE: 4

Gly Glu Gln Thr Lys Ala Leu Val Thr Gln Leu Thr Leu Phe Asn Gln
1               5                   10                  15

Ile Leu Val Glu Leu Arg Asp Asp Ile Arg Asp Gln Val Lys Glu Met
                20                  25                  30

Ser Leu Ile Arg Asn Thr Ile Met Glu Cys Gln Val Cys Gly
            35                  40                  45

<210> SEQ ID NO 5
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is hydroxyproline

<400> SEQUENCE: 5

Gly Phe Xaa Gly Glu Arg
1               5

<210> SEQ ID NO 6
<211> LENGTH: 24
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is hydroxyproline
<220> FEATURE:
<221> NAME/KEY: MISC_FEATURE
<222> LOCATION: (6)..(6)
<223> OTHER INFORMATION: X is hydroxyproline
<220> FEATURE:
<221> NAME/KEY: MISC_FEATURE
<222> LOCATION: (9)..(9)
<223> OTHER INFORMATION: X is hydroxyproline
<220> FEATURE:
<221> NAME/KEY: MISC_FEATURE
<222> LOCATION: (18)..(18)
<223> OTHER INFORMATION: X is hydroxyproline
<220> FEATURE:
<221> NAME/KEY: MISC_FEATURE
<222> LOCATION: (21)..(21)
<223> OTHER INFORMATION: X is hydroxyproline
<220> FEATURE:
<221> NAME/KEY: MISC_FEATURE
<222> LOCATION: (21)..(1)
<223> OTHER INFORMATION: X is hydroxyproline

```
<220> FEATURE:
<221> NAME/KEY: MISC_FEATURE
<222> LOCATION: (24)..(24)
<223> OTHER INFORMATION: X is hydroxyproline

<400> SEQUENCE: 6

Gly Pro Xaa Gly Pro Xaa Gly Pro Xaa Gly Glu Lys Gly Glu Arg Gly
1               5                   10                  15

Pro Xaa Gly Pro Xaa Gly Pro Xaa
            20

<210> SEQ ID NO 7
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: X is hydroxyproline
<220> FEATURE:
<221> NAME/KEY: MISC_FEATURE
<222> LOCATION: (3)..(3)
<223> OTHER INFORMATION: X is hydroxyproline
<220> FEATURE:
<221> NAME/KEY: MISC_FEATURE
<222> LOCATION: (6)..(6)
<223> OTHER INFORMATION: X is hydroxyproline
<220> FEATURE:
<221> NAME/KEY: MISC_FEATURE
<222> LOCATION: (9)..(9)
<223> OTHER INFORMATION: X is hydroxyproline
<220> FEATURE:
<221> NAME/KEY: MISC_FEATURE
<222> LOCATION: (12)..(12)
<223> OTHER INFORMATION: X is hydroxyproline
<220> FEATURE:
<221> NAME/KEY: MISC_FEATURE
<222> LOCATION: (21)..(21)
<223> OTHER INFORMATION: X is hydroxyproline
<220> FEATURE:
<221> NAME/KEY: MISC_FEATURE
<222> LOCATION: (24)..(24)
<223> OTHER INFORMATION: X is hydroxyproline
<220> FEATURE:
<221> NAME/KEY: MISC_FEATURE
<222> LOCATION: (27)..(27)
<223> OTHER INFORMATION: X is hydroxyproline
<220> FEATURE:
<221> NAME/KEY: MISC_FEATURE
<222> LOCATION: (30)..(30)
<223> OTHER INFORMATION: X is hydroxyproline

<400> SEQUENCE: 7

Gly Pro Xaa Gly Pro Xaa Gly Pro Xaa Gly Pro Xaa Gly Glu Lys Gly
1               5                   10                  15

Glu Arg Gly Pro Xaa Gly Pro Xaa Gly Pro Xaa Gly Pro Xaa
            20                  25                  30

<210> SEQ ID NO 8
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: X is hydroxyproline.
<220> FEATURE:
<221> NAME/KEY: MISC_FEATURE
<222> LOCATION: (3)..(3)
<223> OTHER INFORMATION: X is hydroxyproline.
```

```
<220> FEATURE:
<221> NAME/KEY: MISC_FEATURE
<222> LOCATION: (6)..(6)
<223> OTHER INFORMATION: X is hydroxyproline.
<220> FEATURE:
<221> NAME/KEY: MISC_FEATURE
<222> LOCATION: (9)..(9)
<223> OTHER INFORMATION: X is hydroxyproline.
<220> FEATURE:
<221> NAME/KEY: MISC_FEATURE
<222> LOCATION: (12)..(12)
<223> OTHER INFORMATION: X is hydroxyproline.
<220> FEATURE:
<221> NAME/KEY: MISC_FEATURE
<222> LOCATION: (15)..(15)
<223> OTHER INFORMATION: X is hydroxyproline.
<220> FEATURE:
<221> NAME/KEY: MISC_FEATURE
<222> LOCATION: (21)..(21)
<223> OTHER INFORMATION: X is hydroxyproline.
<220> FEATURE:
<221> NAME/KEY: MISC_FEATURE
<222> LOCATION: (24)..(24)
<223> OTHER INFORMATION: X is hydroxyproline.
<220> FEATURE:
<221> NAME/KEY: MISC_FEATURE
<222> LOCATION: (27)..(27)
<223> OTHER INFORMATION: X is hydroxyproline.
<220> FEATURE:
<221> NAME/KEY: MISC_FEATURE
<222> LOCATION: (30)..(30)
<223> OTHER INFORMATION: X is hydroxyproline.

<400> SEQUENCE: 8

Gly Pro Xaa Gly Pro Xaa Gly Pro Xaa Gly Pro Xaa Gly Phe Xaa Gly
1               5                  10                  15

Glu Arg Gly Pro Xaa Gly Pro Xaa Gly Pro Xaa Gly Pro Xaa
            20                  25                  30

<210> SEQ ID NO 9
<211> LENGTH: 36
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is hydroxyproline
<220> FEATURE:
<221> NAME/KEY: MISC_FEATURE
<222> LOCATION: (6)..(6)
<223> OTHER INFORMATION: X is hydroxyproline
<220> FEATURE:
<221> NAME/KEY: MISC_FEATURE
<222> LOCATION: (9)..(9)
<223> OTHER INFORMATION: X is hydroxyproline
<220> FEATURE:
<221> NAME/KEY: MISC_FEATURE
<222> LOCATION: (12)..(12)
<223> OTHER INFORMATION: X is hydroxyproline
<220> FEATURE:
<221> NAME/KEY: MISC_FEATURE
<222> LOCATION: (15)..(15)
<223> OTHER INFORMATION: X is hydroxyproline
<220> FEATURE:
<221> NAME/KEY: MISC_FEATURE
<222> LOCATION: (24)..(24)
<223> OTHER INFORMATION: X is hydroxyproline
<220> FEATURE:
<221> NAME/KEY: MISC_FEATURE
<222> LOCATION: (27)..(27)
<223> OTHER INFORMATION: X is hydroxyproline
```

```
<220> FEATURE:
<221> NAME/KEY: MISC_FEATURE
<222> LOCATION: (30)..(30)
<223> OTHER INFORMATION: X is hydroxyproline
<220> FEATURE:
<221> NAME/KEY: MISC_FEATURE
<222> LOCATION: (33)..(33)
<223> OTHER INFORMATION: X is hydroxyproline
<220> FEATURE:
<221> NAME/KEY: MISC_FEATURE
<222> LOCATION: (36)..(36)
<223> OTHER INFORMATION: X is hydroxyproline

<400> SEQUENCE: 9

Gly Pro Xaa Gly Pro Xaa Gly Pro Xaa Gly Pro Xaa Gly Pro Xaa Gly
1               5                   10                  15

Glu Lys Gly Glu Arg Gly Pro Xaa Gly Pro Xaa Gly Pro Xaa Gly Pro
            20                  25                  30

Xaa Gly Pro Xaa
        35

<210> SEQ ID NO 10
<211> LENGTH: 24
<212> TYPE: PRT
<213> ORGANISM: Artificial Sequence
<220> FEATURE:
<223> OTHER INFORMATION: Synthetic

<400> SEQUENCE: 10

Gly Pro Pro Gly Pro Pro Gly Pro Pro Gly Glu Lys Gly Glu Arg Gly
1               5                   10                  15

Pro Pro Gly Pro Pro Gly Pro Pro
            20

<210> SEQ ID NO 11
<211> LENGTH: 30
<212> TYPE: PRT
<213> ORGANISM: Artificial Sequence
<220> FEATURE:
<223> OTHER INFORMATION: Synthetic

<400> SEQUENCE: 11

Gly Pro Pro Gly Pro Pro Gly Pro Pro Gly Pro Pro Gly Glu Lys Gly
1               5                   10                  15

Glu Arg Gly Pro Pro Gly Pro Pro Gly Pro Pro Gly Pro Pro
            20                  25                  30

<210> SEQ ID NO 12
<211> LENGTH: 36
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (18)..(18)
<223> OTHER INFORMATION: X is hydroxyproline

<400> SEQUENCE: 12

Gly Pro Pro Gly Pro Pro Gly Pro Pro Gly Pro Pro Gly Pro Pro Gly
1               5                   10                  15

Phe Xaa Gly Glu Arg Gly Pro Pro Gly Pro Pro Gly Pro Pro Gly Pro
            20                  25                  30

Pro Gly Pro Pro
        35
```

```
<210> SEQ ID NO 13
<211> LENGTH: 33
<212> TYPE: PRT
<213> ORGANISM: Artificial Sequence
<220> FEATURE:
<223> OTHER INFORMATION: Synthetic

<400> SEQUENCE: 13

Lys Leu Lys Glu Leu Lys Ser Lys Leu Lys Glu Leu Leu Lys Leu Glu
1               5                   10                  15

Leu Gln Ala Ile Lys Gln Tyr Lys Glu Leu Lys Ala Glu Lys Leu Glu
            20                  25                  30

Leu

<210> SEQ ID NO 14
<211> LENGTH: 21
<212> TYPE: PRT
<213> ORGANISM: Artificial Sequence
<220> FEATURE:
<223> OTHER INFORMATION: Synthetic

<400> SEQUENCE: 14

Leu Lys Ala Leu Glu Glu Lys Leu Lys Ala Leu Glu Glu Lys Leu Lys
1               5                   10                  15

Ala Leu Glu Glu Lys
            20

<210> SEQ ID NO 15
<211> LENGTH: 33
<212> TYPE: PRT
<213> ORGANISM: Artificial Sequence
<220> FEATURE:
<223> OTHER INFORMATION: Synthetic

<400> SEQUENCE: 15

Arg Met Lys Gln Ile Glu Asp Lys Leu Glu Glu Ile Leu Ser Lys Leu
1               5                   10                  15

Tyr His Ile Glu Asn Glu Leu Ala Arg Ile Lys Lys Leu Leu Gly Glu
            20                  25                  30

Arg

<210> SEQ ID NO 16
<211> LENGTH: 46
<212> TYPE: PRT
<213> ORGANISM: Artificial Sequence
<220> FEATURE:
<223> OTHER INFORMATION: Synthetic

<400> SEQUENCE: 16

Ser Asp Leu Gly Pro Gln Met Leu Arg Glu Leu Gln Glu Thr Asn Ala
1               5                   10                  15

Ala Leu Gln Asp Val Arg Asp Trp Leu Arg Gln Val Arg Glu Ile
            20                  25                  30

Thr Phe Leu Lys Asn Thr Val Met Glu Cys Asp Ala Cys Gly
        35                  40                  45

<210> SEQ ID NO 17
<211> LENGTH: 33
<212> TYPE: PRT
<213> ORGANISM: Artificial Sequence
<220> FEATURE:
<223> OTHER INFORMATION: Synthetic
```

```
<400> SEQUENCE: 17

Thr Gln Glu Asp Leu Leu Lys Lys Ile Met Lys Leu Leu Lys Lys Gln
1               5                   10                  15

Ile Lys Leu Leu Lys Lys Gln Ile Lys Met Leu Lys Arg Leu Glu Lys
                20                  25                  30

Gln

<210> SEQ ID NO 18
<211> LENGTH: 15
<212> TYPE: PRT
<213> ORGANISM: Artificial Sequence
<220> FEATURE:
<223> OTHER INFORMATION: Synthetic

<400> SEQUENCE: 18

Val Pro Gly Phe Gly Val Pro Gly Phe Gly Val Pro Gly Phe Gly
1               5                   10                  15

<210> SEQ ID NO 19
<211> LENGTH: 20
<212> TYPE: PRT
<213> ORGANISM: Artificial Sequence
<220> FEATURE:
<223> OTHER INFORMATION: Synthetic

<400> SEQUENCE: 19

Val Pro Gly Phe Gly Val Pro Gly Phe Gly Val Pro Gly Phe Gly Val
1               5                   10                  15

Pro Gly Phe Gly
                20

<210> SEQ ID NO 20
<211> LENGTH: 25
<212> TYPE: PRT
<213> ORGANISM: Artificial Sequence
<220> FEATURE:
<223> OTHER INFORMATION: Synthetic

<400> SEQUENCE: 20

Val Pro Gly Phe Gly Val Pro Gly Phe Gly Val Pro Gly Phe Gly Val
1               5                   10                  15

Pro Gly Phe Gly Val Pro Gly Phe Gly
                20                  25

<210> SEQ ID NO 21
<211> LENGTH: 30
<212> TYPE: PRT
<213> ORGANISM: Artificial Sequence
<220> FEATURE:
<223> OTHER INFORMATION: Synthetic

<400> SEQUENCE: 21

Val Pro Gly Phe Gly Val Pro Gly Phe Gly Val Pro Gly Phe Gly Val
1               5                   10                  15

Pro Gly Phe Gly Val Pro Gly Phe Gly Val Pro Gly Phe Gly
                20                  25                  30

<210> SEQ ID NO 22
<211> LENGTH: 5
<212> TYPE: PRT
<213> ORGANISM: Artificial Sequence
<220> FEATURE:
<223> OTHER INFORMATION: Synthetic
```

```
<220> FEATURE:
<221> NAME/KEY: MISC_FEATURE
<222> LOCATION: (4)..(4)
<223> OTHER INFORMATION: X is hydroxyproline

<400> SEQUENCE: 22

Val Pro Gly Xaa Gly
1               5

<210> SEQ ID NO 23
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: X is hydroxyproline
<220> FEATURE:
<221> NAME/KEY: MISC_FEATURE
<222> LOCATION: (9)..(9)
<223> OTHER INFORMATION: X is hydroxyproline
<220> FEATURE:
<221> NAME/KEY: MISC_FEATURE
<222> LOCATION: (14)..(14)
<223> OTHER INFORMATION: X is hydroxyproline

<400> SEQUENCE: 23

Val Pro Gly Xaa Gly Val Pro Gly Xaa Gly Val Pro Gly Xaa Gly
1               5                   10                  15

<210> SEQ ID NO 24
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: X is hydroxyproline
<220> FEATURE:
<221> NAME/KEY: MISC_FEATURE
<222> LOCATION: (9)..(9)
<223> OTHER INFORMATION: X is hydroxyproline
<220> FEATURE:
<221> NAME/KEY: MISC_FEATURE
<222> LOCATION: (14)..(14)
<223> OTHER INFORMATION: X is hydroxyproline
<220> FEATURE:
<221> NAME/KEY: MISC_FEATURE
<222> LOCATION: (19)..(19)
<223> OTHER INFORMATION: X is hydroxyproline

<400> SEQUENCE: 24

Val Pro Gly Xaa Gly Val Pro Gly Xaa Gly Val Pro Gly Xaa Gly Val
1               5                   10                  15

Pro Gly Xaa Gly
            20

<210> SEQ ID NO 25
<211> LENGTH: 25
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: X is hydroxyproline
```

```
<220> FEATURE:
<221> NAME/KEY: MISC_FEATURE
<222> LOCATION: (9)..(9)
<223> OTHER INFORMATION: X is hydroxyproline
<220> FEATURE:
<221> NAME/KEY: MISC_FEATURE
<222> LOCATION: (14)..(14)
<223> OTHER INFORMATION: X is hydroxyproline
<220> FEATURE:
<221> NAME/KEY: MISC_FEATURE
<222> LOCATION: (19)..(19)
<223> OTHER INFORMATION: X is hydroxyproline
<220> FEATURE:
<221> NAME/KEY: MISC_FEATURE
<222> LOCATION: (24)..(24)
<223> OTHER INFORMATION: X is hydroxyproline

<400> SEQUENCE: 25

Val Pro Gly Xaa Gly Val Pro Gly Xaa Gly Val Pro Gly Xaa Gly Val
1               5                   10                  15

Pro Gly Xaa Gly Val Pro Gly Xaa Gly
            20                  25

<210> SEQ ID NO 26
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: X is hydroxyproline
<220> FEATURE:
<221> NAME/KEY: MISC_FEATURE
<222> LOCATION: (9)..(9)
<223> OTHER INFORMATION: X is hydroxyproline
<220> FEATURE:
<221> NAME/KEY: MISC_FEATURE
<222> LOCATION: (14)..(14)
<223> OTHER INFORMATION: X is hydroxyproline
<220> FEATURE:
<221> NAME/KEY: MISC_FEATURE
<222> LOCATION: (19)..(19)
<223> OTHER INFORMATION: X is hydroxyproline
<220> FEATURE:
<221> NAME/KEY: MISC_FEATURE
<222> LOCATION: (24)..(24)
<223> OTHER INFORMATION: X is hydroxyproline
<220> FEATURE:
<221> NAME/KEY: MISC_FEATURE
<222> LOCATION: (29)..(29)
<223> OTHER INFORMATION: X is hydroxyproline

<400> SEQUENCE: 26

Val Pro Gly Xaa Gly Val Pro Gly Xaa Gly Val Pro Gly Xaa Gly Val
1               5                   10                  15

Pro Gly Xaa Gly Val Pro Gly Xaa Gly Val Pro Gly Xaa Gly
            20                  25                  30

<210> SEQ ID NO 27
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is hydroxyproline
```

```
<400> SEQUENCE: 27

Xaa Pro Ala Val Gly
1               5

<210> SEQ ID NO 28
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is hydroxyproline

<400> SEQUENCE: 28

Xaa Pro Gly Val Gly
1               5

<210> SEQ ID NO 29
<211> LENGTH: 24
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(24)
<223> OTHER INFORMATION: X is hydroxyproline
<220> FEATURE:
<221> NAME/KEY: MISC_FEATURE
<222> LOCATION: (3)..(3)
<223> OTHER INFORMATION: X is hydroxyproline
<220> FEATURE:
<221> NAME/KEY: MISC_FEATURE
<222> LOCATION: (6)..(6)
<223> OTHER INFORMATION: X is hydroxyproline
<220> FEATURE:
<221> NAME/KEY: MISC_FEATURE
<222> LOCATION: (9)..(9)
<223> OTHER INFORMATION: X is hydroxyproline
<220> FEATURE:
<221> NAME/KEY: MISC_FEATURE
<222> LOCATION: (12)..(12)
<223> OTHER INFORMATION: X is hydroxyproline
<220> FEATURE:
<221> NAME/KEY: MISC_FEATURE
<222> LOCATION: (18)..(18)
<223> OTHER INFORMATION: X is hydroxyproline
<220> FEATURE:
<221> NAME/KEY: MISC_FEATURE
<222> LOCATION: (21)..(21)
<223> OTHER INFORMATION: X is hydroxyproline
<220> FEATURE:
<221> NAME/KEY: MISC_FEATURE
<222> LOCATION: (24)..(24)
<223> OTHER INFORMATION: X is hydroxyproline

<400> SEQUENCE: 29

Gly Pro Xaa Gly Pro Xaa Gly Pro Xaa Gly Phe Xaa Gly Glu Arg Gly
1               5                   10                  15

Pro Xaa Gly Pro Xaa Gly Pro Xaa
            20

<210> SEQ ID NO 30
<211> LENGTH: 36
<212> TYPE: PRT
<213> ORGANISM: Artificial Sequence
<220> FEATURE:
<223> OTHER INFORMATION: Synthetic
```

```
<220> FEATURE:
<221> NAME/KEY: MISC_FEATURE
<222> LOCATION: (3)..(3)
<223> OTHER INFORMATION: X is hydroxyproline
<220> FEATURE:
<221> NAME/KEY: MISC_FEATURE
<222> LOCATION: (6)..(6)
<223> OTHER INFORMATION: X is hydroxyproline
<220> FEATURE:
<221> NAME/KEY: MISC_FEATURE
<222> LOCATION: (9)..(9)
<223> OTHER INFORMATION: X is hydroxyproline
<220> FEATURE:
<221> NAME/KEY: MISC_FEATURE
<222> LOCATION: (12)..(12)
<223> OTHER INFORMATION: X is hydroxyproline
<220> FEATURE:
<221> NAME/KEY: MISC_FEATURE
<222> LOCATION: (15)..(15)
<223> OTHER INFORMATION: X is hydroxyproline
<220> FEATURE:
<221> NAME/KEY: MISC_FEATURE
<222> LOCATION: (18)..(18)
<223> OTHER INFORMATION: X is hydroxyproline
<220> FEATURE:
<221> NAME/KEY: MISC_FEATURE
<222> LOCATION: (24)..(24)
<223> OTHER INFORMATION: X is hydroxyproline
<220> FEATURE:
<221> NAME/KEY: MISC_FEATURE
<222> LOCATION: (27)..(27)
<223> OTHER INFORMATION: X is hydroxyproline
<220> FEATURE:
<221> NAME/KEY: MISC_FEATURE
<222> LOCATION: (30)..(30)
<223> OTHER INFORMATION: X is hydroxyproline
<220> FEATURE:
<221> NAME/KEY: MISC_FEATURE
<222> LOCATION: (33)..(33)
<223> OTHER INFORMATION: X is hydroxyproline
<220> FEATURE:
<221> NAME/KEY: MISC_FEATURE
<222> LOCATION: (36)..(36)
<223> OTHER INFORMATION: X is hydroxyproline

<400> SEQUENCE: 30

Gly Pro Xaa Gly Pro Xaa Gly Pro Xaa Gly Pro Xaa Gly Pro Xaa Gly
1               5                   10                  15

Phe Xaa Gly Glu Arg Gly Pro Xaa Gly Pro Xaa Gly Pro Xaa Gly Pro
            20                  25                  30

Xaa Gly Pro Xaa
        35

<210> SEQ ID NO 31
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (15)..(15)
<223> OTHER INFORMATION: X is hydroxyproline

<400> SEQUENCE: 31

Gly Pro Pro Gly Pro Pro Gly Pro Pro Gly Pro Pro Gly Phe Xaa Gly
1               5                   10                  15

Glu Arg Gly Pro Pro Gly Pro Pro Gly Pro Pro Gly Pro Pro
            20                  25                  30
```

THERMORESPONSIVE BIOCONJUGATES AND THEIR CONTROLLED DELIVERY OF CARGO

CROSS-REFERENCE TO RELATED APPLICATION

This application is a U.S. national phase application of International Application No. PCT/US2016/044917, filed Jul. 29, 2016, claiming the benefit of U.S. Provisional Application No. 62/198,193, filed Jul. 29, 2015, and U.S. Provisional Application No. 62/315,079, filed Mar. 30, 2016, the contents of each of which are incorporated herein by reference in their entireties for all purposes.

REFERENCE TO U.S. GOVERNMENT SUPPORT

This work is supported by grants from the National Science Found (NSF) (Grant #DMR 0907478). The United States has certain rights in the invention.

The Sequence Listing for this application is labeled "UOD-459US_SequenceListing_ST25," which was created on Nov. 4, 2019 and is 16.4 KB. The entire content of the sequence listing is incorporated herein by reference in its entirety.

FIELD OF THE INVENTION

The invention relates generally to bioconjugates, their targeting to select materials, matrices and tissues, and controlled delivery of cargo carried by the bioconjugates.

BACKGROUND OF THE INVENTION

In the past few decades, thermoresponsive polymers have been intensely studied to develop new smart materials such as hydrogels, films, and drug nanocarriers. Elastin-like polypeptides (ELPs), in particular, which are derived from the hydrophobic domain of tropoelastin and comprise many copies of the pentapeptide repeat Val-Pro-Gly-Xaa-Gly (VPGXG; SEQ ID NO: 22), have also been very widely studied owing to their LCST-like behavior. With heating above their inverse transition temperature ($T_t$), the ELPs collapse into a coacervate phase, enabling their use as building blocks for temperature-sensitive smart biomaterials. Many studies have demonstrated the outstanding versatility of the (VPGXG)$_n$ (VPGXG; SEQ ID NO: 22) consensus repeat for modulating inverse transition temperatures and in the formation of a range of drug delivery vehicles that can be targeted to matrices, tissues and cells either via passive or peptide- and stimuli-responsive mechanisms. The inverse temperature transition can also be triggered by cations, such as $Ca^{2+}$, or other ligands, via functionalization of the ELP with a ligand-binding domain. While these studies illustrate the utility of the ELPs, essentially all of the ELPs employed have been recombinant, comprising generally on the order of fifty and even hundreds of pentapeptide repeats. Short synthetic ELPs (e.g., those with fewer than ten pentapeptides) have not been used widely for the thermoresponsive fabrication of nanoparticles, owing to their high transition temperatures. In addition, while many hydrogels and films have been produced from ELPs combined with domains of other structural proteins such as silk and resilin, there have been no reports of short ELP-based nanostructures equipped with such domains.

Short synthetic collagen-like peptides (CLPs), similarly, have been employed widely in studies aimed at collagen folding and at development of therapeutic matrices and molecules. CLPs have been shown to mimic the triple helix conformation of native collagen, and thus have served as model systems for triple helix structure and the stabilization effect of specific amino acid residues in collagens, as well as to mimic collagen fibril formation. Additionally, recent studies have illustrated that single-stranded CLPs have a strong propensity to bind native collagen via a strand invasion process. The high propensity of CLPs for collagen permits detection of minute quantities of collagen (e.g., 5 ng) with substantial promise for staining collagens in human tissues (e.g., skin; cornea; bone; liver), especially those with high ECM turnover (e.g., prostate tumor xenografts, joints, and articular cartilage). Despite this widespread use, the utilization of CLPs as domains in responsive nanoparticles has been described in only a very limited number of reports.

There remains a need for thermoresponsive bioconjugates capable of controlled delivery to target matrices and tissues, and selecting thermoresponsive conjugates having unanticipated properties to enable such delivery.

SUMMARY OF THE INVENTION

The present invention relates to bioconjugates and delivery thereof.

A method for delivering a bioconjugate to a target matrix is provided. The method comprises (a) introducing a bioconjugate self-assembled into particles to a target matrix, wherein the bioconjugate comprises a first molecule comprising an elastin-like peptide (ELP), a second molecule capable of self-associating into an oligomer, and a linker connecting the first molecule with the second molecule, and (b) increasing the temperature of the target matrix to disassemble the particles at the target matrix.

According the method of the present invention, step (a) may be carried out at 35-39° C. Step (a) is carried out at 37° C., and the temperature of the target matrix is increased to at least 43° C. in step (b).

According the method of the present invention, the ELP may comprise 3-25 repeats of VPGXG (SEQ ID NO: 22), XPGVG (SEQ ID NO: 28) or XPAVG (SEQ ID NO: 27), wherein X is an amino acid. The ELP may be VPGXGVPGXGVPGXG (SEQ ID NO: 23), VPGXGVPGXGVPGXGVPGXG (SEQ ID NO: 24), VPGXGVPGXGVPGXGVPGXGVPGXG (SEQ ID NO: 25) or VPGXGVPGXGVPGXGVPGXGVPGXGVPGXG (SEQ ID NO: 26), wherein X is an amino acid. The ELP may be VPGFGVPGFGVPGFGVPGFGVPGFGVPGFG (SEQ ID NO: 21).

According the method of the present invention, the second molecule may comprise a peptide. The peptide may be a collagen-like peptide (CLP) or a coiled-coil peptide (CCP).

The CLP may consist of 5-15 repeats of GPO or GPP. The CLP peptide may be selected from the group consisting of GPOGPOGPOFOGERGPOGPOGPO (SEQ ID NO: 29), GPOGPOGPOGPOFOGERGPOGPOGPOGPO (SEQ ID NO: 8), GPOGPOGPOGPOGPOFOGERGPOGPOG-POGPOGPO (SEQ ID NO: 30), GPPGPPGPPGPPGFO-GERGPPGPPGPPGPP (SEQ ID NO: 31), GPPGPPGPPG-PPGPPGFOGERGPPGPPGPPGPPGPP (SEQ ID NO: 12), GPOGPOGPOGEKGERGPOGPOGPO (SEQ ID NO: 6), GPOGPOGPOGPOGEKGERGPOGPOGPOGPO (SEQ ID NO: 7), GPOGPOGPOGPOGPOGEKGERGPOGPOG-POGPOGPO (SEQ ID NO: 9), GPPGPPGPPGEKGERGP- PGPPGPP (SEQ ID NO: 10) and GPPGPPGPPGPPGEK-GERGPPGPPGPPGPP (SEQ ID NO: 11). The CLP may be GPOGPOGPOGPOGFOGERGPOGPOGPOGPO (SEQ ID NO: 8).

The CCP may be selected from the group consisting of

RMKQIEDKLEEILSKLYHIENELARIKKLLGER, (SEQ ID NO: 15)

LKALEEKLKALEEKLKALEEK, (SEQ ID NO: 14)

KLKELKSKLKELLKLELQAIKQYKELKAEKLEL, (SEQ ID NO: 13)

TQEDLLKKIMKLLKKQIKLLKKQIKMLKRLEKQ, (SEQ ID NO: 17)

SDLGPQMLRELQETNAALQDVRDWLRQQVREITFLKNTVMECDACG, (SEQ ID NO: 16)

GEQTKALVTQLTLFNQILVELRDDIRDQVKEMSLIRNTIMECQVCG, (SEQ ID NO: 4)

GDFNRQFLGQMTQLNQLLGEVKDLLRQQVKETSFLRNTIAECQACG, (SEQ ID NO: 3)

ASTDTLQAETDQLEDEKYALQTEIANLLKEKEKLGAP (SEQ ID NO: 2) and

ASIARLEEKVKTLKAQNYELASTANMLREQVAQLGAP. (SEQ ID NO: 1)

According the method of the present invention, the second molecule may comprise a double-stranded DNA.

According the method of the present invention, the linker may be formed by solid phase peptide coupling, Schiff base formation and reduction, azide-alkyne click reaction, Michael-type addition, tetrazine ligation, or Staudinger ligation.

According to the method of the present invention, the bioconjugate may have formula (I):

(I)

In formula (I), the ELP may be VPGFGVPGFGVPGF-GVPGFGVPGFGVPGFG (SEQ ID NO: 21), and the CLP may be GPOGPOGPOGPOGFOGERGPOGPOGPOGPO (SEQ ID NO: 8).

According to the method of the present invention, the particles may have an average particle diameter of 50-200 nm. The particles may be selected from the group consisting of micelles, cylinders, vesicles and structures comprising bilayer membranes. The micelles may have an average particle diameter of 10-50 nm. The cylinders may have an average length of 10 nm-100 μm and an average diameter of 10-50 nm. The vesicles may have an average particle diameter of 20-2000 nm. The bilayer membranes may have an average thickness of 10-50 nm.

The method may further comprise exposing the target matrix to a trigger after step (a) and the trigger may be selected from the group consisting of a decrease in temperature, pH changes, metal ion binding, light exposure, changes in thiol concentration, changes in glutathione concentration or the presence of enzymes.

The method may further comprise decreasing the temperature of the target matrix after step (a). The target matrix may have a pH of 6.5-7.5 in step (a), and the method may further comprise changing the pH of the target matrix after step (a).

The method may further comprise exposing the target matrix to a metal ion after step (a). The method may further comprise exposing the target matrix to light after step (a). The method may further comprise changing thiol concentration of the target matrix after step (a). The method may further comprise changing glutathione concentration of the target matrix after step (a).

The method may further comprise binding the bioconjugate specifically to the target matrix in step (a). The target matrix may be in an organism. The target matrix may comprise collagen. The target matrix may be selected from the group consisting of articular cartilage, osteoarthritic cartilage, rheumatoid arthritis tissues, tumors, skeleton, heart tissues and blood vessels.

According to the method of the present invention, the particles of the bioconjugate may carry a cargo molecule in step (a), and the cargo molecule may be released to the target matrix upon disassembly of the particles. The cargo molecule may be immobilized to the particles in step (a). The target matrix may have a disease or condition, and the cargo molecule may be a therapeutic agent for treating the disease or condition. Upon disassembly of the particles, the cargo molecule may be released to the target matrix in an effective amount for treating the disease or condition. The disease or condition is selected from the group consisting of osteoarthritis, rheumatoid arthritis and cancer.

A bioconjugate is also provided. The bioconjugate comprises a first molecule comprising an elastin-like peptide (ELP), a second molecule capable of self-associating into an oligomer, and a linker connecting the first molecule with the second molecule. The bioconjugate is self-assembled into particles. The particles are disassembled when the temperature is increased.

The bioconjugate may be self-assembled into particles at 35-39° C. The bioconjugate may be self-assembled into particles at 37° C., and the particles may be disassembled when the temperature is increased to at least 43° C.

In the bioconjugate, the ELP may comprise 3-25 repeats of VPGXG (SEQ ID NO: 22), XPGVG (SEQ ID NO: 28) or XPAVG (SEQ ID NO: 27), wherein X is an amino acid. The ELP may be VPGXGVPGXGVPGXG (SEQ ID NO: 23), VPGXGVPGXGVPGXGVPGXG (SEQ ID NO: 24), VPGXGVPGXGVPGXGVPGXGVPGXG (SEQ ID NO: 25) or VPGXGVPGXGVPGXGVPGXGVPGXGVPGXG (SEQ ID NO: 26), wherein X is an amino acid. The ELP may be VPGFGVPGFGVPGFGVPGFGVPGFGVPGFG (SEQ ID NO: 21).

In the bioconjugate, the second molecule may comprise a peptide. The peptide may be a collagen-like peptide (CLP) or a coiled-coil peptide (CCP).

The CLP may consist of 5-15 repeats of GPO or GPP. The CLP peptide may be selected from the group consisting of GPOGPOGPOGFOGERGPOGPOGPO (SEQ ID NO: 29), GPOGPOGPOGPOGFOGERGPOGPOGPOGPO (SEQ ID NO: 8), GPOGPOGPOGPOGPOGFOGERGPOGPOG-POGPOGPO (SEQ ID NO: 30), GPPGPPGPPGPPGFO-GERGPPGPPGPPGPP (SEQ ID NO: 31), GPPGPPGPPG-PPGPPGFOGERGPPGPPGPPGPPGPP (SEQ ID NO: 12), GPOGPOGPOGEKGERGPOGPOGPO (SEQ ID NO: 6), GPOGPOGPOGPOGEKGERGPOGPOGPOGPO (SEQ ID NO: 7), GPOGPOGPOGPOGPOGEKGERGPOGPOG-POGPOGPO (SEQ ID NO: 9), GPPGPPGPPGEKGERGP- PGPPGPP (SEQ ID NO: 10) and GPPGPPGPPGPPGEK-GERGPPGPPGPPGPP (SEQ ID NO: 11). The CLP may be GPOGPOGPOGPOGFOGERGPOGPOGPOGPO (SEQ ID NO: 8).

The CCP may be selected from the group consisting of

RMKQIEDKLEEILSKLYHIENELARIKKLLGER, (SEQ ID NO: 15)

LKALEEKLKALEEKLKALEEK, (SEQ ID NO: 14)

KLKELKSKLKELLKLELQAIKQYKELKAEKLEL, (SEQ ID NO: 13)

TQEDLLKKIMKLLKKQIKLLKKQIKMLKRLEKQ, (SEQ ID NO: 17)

SDLGPQMLRELQETNAALQDVRDWLRQQVREITFLKNIVMECDACG, (SEQ ID NO: 16)

GEQTKALVTQLTLFNQILVELRDDIRDQVKEMSLIRNTIMECQVCG, (SEQ ID NO: 4)

GDFNRQFLGQMTQLNQLLGEVKDLLRQQVKETSFLRNTIAECQACG, (SEQ ID NO: 3)

ASTDTLQAETDQLEDEKYALQTEIANLLKEKEKLGAP (SEQ ID NO: 2)
and

ASIARLEEKVKTLKAQNYELASTANMLREQVAQLGAP. (SEQ ID NO: 1)

In the bioconjugate, the second molecule may comprise a double-stranded DNA.

In the bioconjugate, the linker may be formed by solid phase peptide coupling, Schiff base formation and reduction, azide-alkyne click reaction, Michael-type addition, tetrazine ligation, or Staudinger ligation.

The bioconjugate may have formula (I):

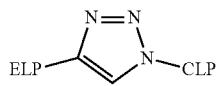

(I)

In formula (I), the ELP may be VPGFGVPGFGVPGF-GVPGFGVPGFGVPGFG (SEQ ID NO: 21), and the CLP may be GPOGPOGPOGPOGFOGERGPOGPOGPOGPO (SEQ ID NO: 8).

The particles of the bioconjugate may have an average particle size of 50-200 nm. The particles may be selected from the group consisting of micelles, cylinders, vesicles and bilayer membranes. The micelles may have an average particle diameter of 10-50 nm. The cylinders may have an average length of 10 nm-100 µm and an average diameter of 10-50 nm. The vesicles may have an average particle diameter of 20-2000 nm. The bilayer membranes may have an average thickness of 10-50 nm.

The particles of the bioconjugate may be bound specifically to a target matrix. The target matrix may be in an organism. The target matrix may comprise collagen. The target matrix may be selected from the group consisting of articular cartilage, osteoarthritic cartilage, rheumatoid arthritis tissues, tumors, skeleton, heart tissues and blood vessels. The particles of the bioconjugate may carry a cargo molecule, and the cargo molecule may be released to the target matrix upon disassembly of the particles. The cargo molecule may be immobilized to the particles. The target matrix may have a disease or condition and wherein the cargo molecule is a therapeutic agent for treating the disease or condition. Upon disassembly of the particles, the cargo molecule may be released to the target matrix in an effective amount for treating the disease or condition in the target tissue. The disease or condition may be selected from the group consisting of osteoarthritis, rheumatoid arthritis and cancer. The target matrix may be exposed to a trigger selected from the group consisting of a decrease in temperature, pH changes, metal ion binding, light exposure, changes in thiol concentration, changes in glutathione concentration or the presence of enzymes.

DETAILED DESCRIPTION OF THE INVENTION

Figure 1:
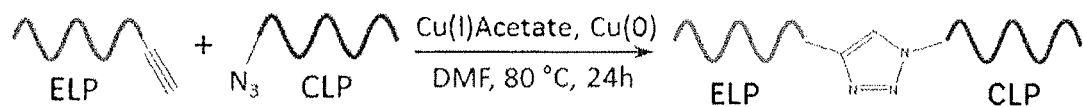
FIG. 1 illustrates Scheme 1, chemical conjugation of ELP and CLP.

The present invention relates to thermoresponsive bioconjugates and controlled delivery of the bioconjugates and encapsulated cargo to a target matrix (e.g., tissues, organisms, synthetic materials, biomaterials, and organic/inorganic samples). The bioconjugates of the present invention self-assemble into particles, which become disassembled upon an increase of temperature. The thermoresponsiveness and target specificity of the bioconjugates may be controlled by modifying the components (e.g., biological molecules and chemical compounds) of the bioconjugates and/or applying different triggers to the bioconjugates. The bioconjugates of the present invention are capable of being targeted to desirable locations, for example, tissues, organisms, materials, or other organic/inorganic matter, which enables delivery of cargo molecules to the desirable locations by simple thermal control.

The term "bioconjugate" used herein refers to a conjugate comprising two or more biological molecules linked together directly or via a linker. The biological molecules may be peptides, nucleic acids, carbohydrates, lipids or combinations thereof.

The term "peptide" used herein refers to a compound comprising amino acids with no limitation with respect to the minimum number of amino acids. The peptide may have about 5-50 amino acids, for example, no more than about 250 amino acids. A peptide may comprise two or more repeats of one or more short amino acid sequences. Such a short amino acid sequence may have about 3-25 amino acids. There may be no, one or more amino acids between the repeats. The amino acid may be natural or synthetic/non-natural. The peptide may be natural or synthetic.

The term "thermoresponsive" used herein refers to the ability of a bioconjugate or molecule to change its structure or activity when the temperature is changed. For example, a thermoresponsive bioconjugate or molecule may change from an insoluble structure to a soluble structure when the temperature is increased.

The terms "self-assembled," "self-assembly," "self-associated" or "self-association" are used herein interchangeably and refer to forming or formation of a structure by a bioconjugate or a molecule by itself under certain conditions, for example, under a physiological condition. Upon self-assembly or self-association, the bioconjugate or molecule may assemble and/or become insoluble in water, for example, showing an assembly concentration or water solubility of no more than 10, 1, 0.1 0.01 or 0.001 mg/mL.

The terms "disassembled," "disassembly," "disassociated" or "disassociation" are used herein interchangeably and refer to the disappearance or loss of a structure formed by a bioconjugate or a molecule due to, for example, deviation from physiological conditions.

Upon disassembly or disassociation, the bioconjugate or molecule may disperse in or become soluble in water, for example, showing water solubility of at least 10, 1, 0.1, 0.01 or 0.001 mg/mL.

The term "physiological condition" used herein refers to a condition naturally occurring, for example, in or surrounding a target matrix (e.g., an organism or tissue). The physiological condition may comprise a physiological temperature, a physiological pH or a combination thereof. In humans, the physiological temperature may be about 35-39° C. (e.g., about 37° C.), and the physiological pH may be about 6.5-7.5 (e.g., about 7.0).

The term "organism" used herein refers to an individual living thing, for example, an animal or plant. The organism may be a mammal (e.g., human).

The term "tissue" used herein refers to a material of which of an organism is made. The tissue may be a natural tissue in or isolated from an organism, an artificial tissue obtained by modifying a natural tissue or prepared chemically or recombinantly, or a combination thereof. The tissue may comprise collagen. Exemplary tissues include articular cartilage, osteoarthritic cartilage, rheumatoid arthritis tissues, tumors, skeleton, heart tissues and blood vessels.

The term "matrix" used herein refers to a material comprising at least one specialized material. The specialized material may be derived from synthetic polymers, from materials isolated from extracellular matrix or tissue, or any other strategy known in the art for generating a matrix. The matrix may be a natural matrix in or isolated from an organism, an artificial matrix obtained by modifying a natural tissue or prepared chemically or recombinantly, or a combination thereof. The matrix may be made of an organic material, an inorganic material or a combination thereof. The matrix may be a tissue, an organism or soil.

The term "target matrix" used herein refers to a desirable matrix to which a bioconjugate is delivered or intended to be delivered. The target matrix may be made of an organic material, an inorganic material or a combination thereof. The target matrix may be a natural tissue in an organism or isolated from an organism. The target matrix may be an artificial tissue. The target matrix may be a combination of natural and artificial tissues. The target matrix may comprise collagen. Exemplary target matrices include articular cartilage, osteoarthritic cartilage, rheumatoid arthritis tissues, tumors, skeleton, heart tissues and blood vessels.

The term "particles" used herein refers to a mass, solid or hollow. The mass may be insoluble in water and have water solubility of no more than about of no more than 10, 1, 0.1, 0.01 or 0.001 mg/mL. The particles may be detected by conventional techniques known in the art, for example, light scattering. The particles may have an average size of about 1-1,000,000 nm, for example, about 1-500,000 nm, 1-100,000 nm, 1-5,000 nm, 1-2,000 nm, 1-1,000 nm, 1-500 nm, 1-200 nm, 1-100 nm, 1-50 nm, 10-50 nm, or 10-40 nm.

The particles may be micelles, cylinders, vesicles, structures comprising bilayer membranes or combinations thereof. The micelles may have an average particle diameter of 10-40 nm. The cylinders may have an average length of 10 nm-100 μm and an average diameter of 10-40 nm. The vesicles may have an average particle diameter of 20-2000 nm. The bilayer membranes may have an average thickness of 10-40 nm.

The term "cargo molecule" used herein refers to any biological molecule, chemical compound or a combination thereof. The cargo molecule may be hydrophobic or hydrophilic. The cargo molecule may be carried by a bioconjugate and delivered to a target matrix.

The cargo molecule may be a therapeutic agent. The therapeutic agent may be a drug for treating or preventing a disease or condition at a target matrix. The disease or condition may be osteoarthritis (OA) or rheumatoid arthritis. The cargo molecule may be a non-steroidal anti-inflammatory drug (NSAID). The NSAID may be selected from the group consisting of certain salicylates, propionic acid derivatives, acetic acid derivatives, enolic acid (oxicam) derivatives, anthranilic acid derivatives (fenamates), selective COX-2 inhibitors and sulfonanilides, a disease modification drug such as MMP-3 inhibitor II, MMP-3 inhibitor III, Batimastat (BB-94), Ilomastat (GM6001), MMP-13 Inhibitor II or PG530742. The NSAID may also be selected from the group consisting of valdecoxib, ibuprofen, etodolac, meloxicam and naproxen.

The disease or condition may be cancer. The therapeutic agent may be a cancer drug. Exemplary cancer drugs include abiraterone, alemtuzumab, anastrozole, aprepitant, arsenic trioxide, atezolizumab, azacitidine, bevacizumab, bleomycin, bortezomib, cabazitaxel, capecitabine, carboplatin, cetuximab, chemotherapy drug combinations, cisplatin, crizotinib, cyclophosphamide, cytarabine, denosumab, docetaxel, doxorubicin, eribulin, erlotinib, etoposide, everolimus, exemestane, filgrastim, fluorouracil, fulvestrant, gemcitabine, hpv vaccine, imatinib, imiquimod, ipilimumab, ixabepilone, lapatinib, lenalidomide, letrozole, leuprolide, mesna, methotrexate, nivolumab, oxaliplatin, paclitaxel, palonosetron, pembrolizumab, pemetrexed, prednisone, radium-223, rituximab, sipuleucel-t, sorafenib, sunitinib, talc intrapleural, tamoxifen, temozolomide, temsirolimus, thalidomide, trastuzumab, vinorelbine and zoledronic acid.

The term "an effective amount" used herein refers to an amount of an agent (e.g., a cargo molecule or bioconjugate) required to achieve a stated goal (e.g., treating or preventing a disease or condition at, for example, a target matrix. The effective amount of an agent may vary depending upon the stated goals, the physical characteristics of the target matrix, the nature and severity of the goal (e.g., a disease or disorder), the existence of related or unrelated conditions (e.g., medical conditions), the nature of the agent (e.g., a cargo molecule or bioconjugate), the means of application the agent to the target matrix, and the application method. A specific dose for a given agent for a stated goal may generally be set by the judgment of a scientist or physician. The agent may be introduced to the target matrix in one or multiple applications.

The present invention provides a bioconjugate. The bioconjugate comprises a first molecule, a second molecule and a linker connecting the first molecule with the second molecule. The first molecule comprises an elastin-like peptide (ELP). The second molecule is capable of self-associating into an oligomer. The bioconjugate is self-assembled into particles. The particles are disassembled when the temperature is increased.

The ELP may be thermoresponsive and have an inverse transition temperature (lower critical solution-like (LCST-like) temperature of about 4-35° C. The ELP may collapse into a coacervate phase when the temperature is higher than its inverse transition temperature (Tt). In one embodiment, the first molecule is the ELP.

The ELP may have two or more repeats of an amino acid sequence. The repeated amino acid sequence may be at least 2, 3, 4, 5, 6, 7, 8, 9, 10, 20 or 50 amino acids. The repeated amino acid sequence may be no more than 125, 250 or 500 amino acids. The ELP may comprise 3-5, 3-10, 3-25, 3-50 or 3-100 (e.g., 3, 4, 5 or 6) repeats of VPGXG (SEQ ID NO: 22), XPGVG (SEQ ID NO: 28) or XPAVG (SEQ ID NO: 27), in which X may be any amino acid, for example, phenylalanine (F). In the ELP, there may be 0, 1, 2, 3, 4, 5 or more amino acids between the repeated amino acid sequences. The ELP may have no more than 125, 250, 500 or 1000 amino acids. The ELP may comprise an amino acid sequence at least about 80%, 90%, 95%, 99% or 100% identical to VPGXGVPGXGVPGXG (SEQ ID NO: 23), VPGXGVPGXGVPGXGVPGXG (SEQ ID NO: 24), VPGXGVPGXGVPGXGVPGXGVPGXG (SEQ ID NO: 25) or VPGXGVPGXGVPGXGVPGXGVPGXGVPGXG (SEQ ID NO: 26), in which X may be any amino acid, for example, phenylalanine (F). In some embodiments, the ELP is VPGXGVPGXGVPGXG (SEQ ID NO: 23), VPGXGVPGXGVPGXGVPGXG (SEQ ID NO: 24), VPGXGVPGXGVPGXGVPGXGVPGXG (SEQ ID NO: 25) or VPGXGVPGXGVPGXGVPGXGVPGXGVPGXG (SEQ ID NO: 26), in which X may be any amino acid, for example, phenylalanine (F). In one embodiment, the ELP is VPGFGVPGFGVPGFGVPGFGVPGFGVPGFG (SEQ ID NO: 21).

The second molecule may comprise a peptide. The peptide may be any peptide capable of forming an oligomer. The peptide may form a dimer, trimer, tetramer or pentamer. The peptide may be natural or synthetic. The peptide may be a collagen-like peptide (CLP) (also known as a collagen-mimetic peptide (CMP)) or a coiled-coil peptide (CCP). In one embodiment, the second molecule is a CLP.

The CLP may form triple helix and bind specifically to collagen. The CLP may have multiple (e.g., 5-15 or 5-20) repeats of GPO or GPP. There may be 0, 1, 2, 3, 4, 5 or more amino acids between the repeated amino acid sequences. The CLP may have no more than 20, 60, or 100 amino acids. The CLP may comprise an amino acid sequence at least about 80%, 90%, 95%, 99% or 100% identical to an amino acid selected from the group consisting of GPOGPOGPOG-FOGERGPOGPOGPO (SEQ ID NO: 29), GPOGPOGPOG-POGFOGERGPOGPOGPOGPO (SEQ ID NO: 8), GPOG- POGPOGPOGPOGFOGERGPOGPOGPOGPO (SEQ ID NO: 30), GPPGPPGPPGPPGFOGERGPPGPPGPPGPP (SEQ ID NO: 31), GPPGPPGPPGPPGPPGFOGERGPPG-PPGPPGPPGPP (SEQ ID NO: 12), GPOGPOGPOGEK-GERGPOGPOGPO (SEQ ID NO: 6), GPOGPOGPOGPO-GEKGERGPOGPOGPOGPO (SEQ ID NO: 7), GPOGPOGPOGPOGPOGEKGERGPOGPOGPOG-POGPO (SEQ ID NO: 9), GPPGPPGPPGEKGERGPPGP-PGPP (SEQ ID NO: 10) and GPPGPPGPPGPPGEKGERG-PPGPPGPPGPP (SEQ ID NO: 11). In some embodiments, the CLP is GPOGPOGPOGFOGERGPOGPOGPO (SEQ ID NO: 29), GPOGPOGPOGPOGFOGERGPOGPOGPOGPO (SEQ ID NO: 8), GPOGPOGPOGPOGPOGFOGERGPOG-POGPOGPOGPO (SEQ ID NO: 30), GPPGPPGPPGPPG-FOGERGPPGPPGPPGPP (SEQ ID NO: 31), GPPGPPGP-PGPPGPPGFOGERGPPGPPGPPGPPGPP (SEQ ID NO: 12), GPOGPOGPOGEKGERGPOGPOGPO (SEQ ID NO: 6), GPOGPOGPOGPOGEKGERGPOGPOGPOGPO (SEQ ID NO: 7), GPOGPOGPOGPOGPOGEKGERGPOGPOG-POGPOGPO (SEQ ID NO: 9), GPPGPPGPPGEKGERGP-PGPPGPP (SEQ ID NO: 10) or GPPGPPGPPGPPGEK-GERGPPGPPGPPGPP (SEQ ID NO: 11). In one embodiment, the CLP is GPOGPOGPOGPOGFOGERG-POGPOGPOGPO (SEQ ID NO: 8).

The CCP may form a dimer, trimer, tetramer or pentamer. The CPP may be derived from the yeast transcription factor GCN4 (GCN) peptides, cartilage oligomeric matrix protein (COMP) proteins, Fos-Jun coiled coils, or any other coiled coil proteins. The CCP may comprise an amino acid sequence at least about 80%, 90%, 95%, 99% or 100% identical to an amino acid sequence selected from the group consisting of RMKQIEDKLEEILSKLYHIENELARIK-KLLGER (SEQ ID NO: 15), LKALEEKLKALEEKLKA-LEEK (SEQ ID NO: 14), KLKELKSKLKELLKLELQAI-KQYKELKAEKLEL (SEQ ID NO: 13), TQEDLLKKIMKLLKKQIKLLKKQIKMLKRLEKQ (SEQ ID NO: 17), SDLGPQMLRELQETNAALQDVRD-WLRQQVREITFLKNTVMECDACG (SEQ ID NO: 16), GEQTKALVTQLTLFNQILVELRDDIRDQVKEMSLIRN-TIMECQVCG (SEQ ID NO: 4), GDFNRQFLGQMTQLN-QLLGEVKDLLRQQVKETSFLRNTIAECQACG (SEQ ID NO: 3), ASTDTLQAETDQLEDEKYALQTEIAN-LLKEKEKLGAP (SEQ ID NO: 2) and ASIARLEEKVK-TLKAQNYELASTANMLREQVAQLGAP (SEQ ID NO: 1). In some embodiments, the CCP is RMKQIEDKLEEIL-SKLYHIENELARIKKLLGER (SEQ ID NO: 15), LKA-LEEKLKALEEKLKALEEK (SEQ ID NO: 14), KLKELK-SKLKELLKLELQAIKQYKELKAEKLEL (SEQ ID NO: 13), TQEDLLKKIMKLLKKQIKLLKKQIKMLKRLEKQ (SEQ ID NO: 17), SDLGPQMLRELQETNAALQDVRD-WLRQQVREITFLKNTVMECDACG (SEQ ID NO: 16), GEQTKALVTQLTLFNQILVELRDDIRDQVKEMSLIRN-TIMECQVCG (SEQ ID NO: 4), GDFNRQFLGQMTQLN-QLLGEVKDLLRQQVKETSFLRNTIAECQACG (SEQ ID NO: 3), ASTDTLQAETDQLEDEKYALQTEIAN-LLKEKEKLGAP (SEQ ID NO: 2) or ASIARLEEKVK-TLKAQNYELASTANMLREQVAQLGAP (SEQ ID NO: 1).

The second molecule may comprise a nucleic acid. For example, the second molecule may comprise a double-stranded DNA. In one embodiment, the second molecule is a double-stranded DNA.

The first and second molecules may be linked by any conventional technique known in the art and by any linker molecules that preserve the ability of the first and second molecules to associate. Linker molecules may be peptide-based or organic molecules. The linker may be formed by any chemical reaction, for example, solid phase peptide coupling, Schiff base formation and reduction, azide-alkyne click reactions, Michael-type addition reactions, tetrazine ligations, or Staudinger ligation (see Table 1).

TABLE 1

| Reactions | Linker formed |
| --- | --- |
| Solid phase peptide coupling | 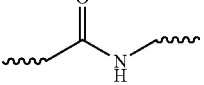 |
| Schiff base formation and reduction | 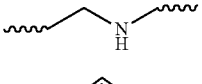 |
| Azide-alkyne click reaction | 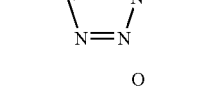 |
| Michael-type addition reaction | 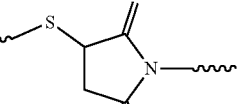 |
| Staudinger ligation | 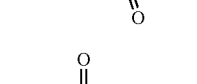 |

In one embodiment, the bioconjugate has formula (I):

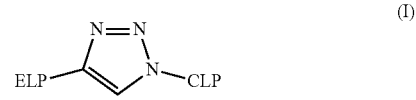

In formula (I), the ELP is VPGFGVPGFGVPGFGVPGF-GVPGFGVPGFG (SEQ ID NO: 21) and the CLP is GPOG-POGPOGPOGFOGERGPOGPOGPOGPO (SEQ ID NO: 8).

The bioconjugate may self-assemble into particles under a physiological condition, for example, at a physiological temperature of 35-39° C. The particles are disassembled when the temperature is increased by at least 1, 2, 3, 4, 5, 10, 20, 40 or 50° C. In one embodiment, the bioconjugate self-assembles into particles at 37° C. and the particles are disassembled when the temperature is increased to at least 43° C. (e.g., 80° C.).

The particles of the bioconjugate may be bound specifically to a target matrix. The target matrix may be a target tissue. The particles of the bioconjugate may be bound specifically to a target tissue. The target tissue may comprise collagen. Exemplary target tissues include articular cartilage, osteoarthritic cartilage, rheumatoid arthritis tissues, tumors, skeleton, heart tissues and blood vessels. The target matrix (e.g., a target tissue) may be exposed to a trigger. The trigger may be a decrease in temperature, pH changes, metal ion binding, light exposure, changes in thiol concentration, changes in glutathione concentration or the presence of enzymes. The light exposure may include irradiation with UV, visible, or near-IR light. Such exposure may stimulate or improve disassembly of the particles bound specifically to the target matrix (e.g., a target tissue).

The particles self-assembled by the bioconjugate may carry a cargo molecule. The cargo molecule may be encapsulated in the particles, for example, in an aqueous lumen of the particles, or embedded within the particles, for example, in the hydrophobic interior part of a bilayer of the particles. The cargo molecule may be immobilized to the particles, for example, attached to the particle chemically or physically. Upon delivery of the bioconjugate in the form of particles to a target matrix or specific binding of the bioconjugate to a target matrix, the cargo molecule may be released to the target matrix upon disassembly of the particles. The target matrix may have a disease or condition, and the cargo molecule may be a therapeutic agent for treating the disease or condition. The released cargo molecule may be in an amount effective for treating the disease or condition. The disease or condition may be osteoarthritis, rheumatoid arthritis or cancer.

The present invention also provides a method for delivering a bioconjugate of the present invention to a target matrix. The delivery method comprises introducing a bioconjugate self-assembled into particles to a target matrix at a desired temperature. Increasing the temperature of the location (e.g., a target tissue, organism or other organic/inorganic matrix) provides a means to disassemble the particles at the target matrix. The bioconjugate comprises a first molecule comprising an elastin-like peptide (ELP), a second molecule capable of self-associating into an oligomer, and a linker connecting the first molecule with the second molecule.

The desired temperature at which the bioconjugate is introduced to the target tissue may be an ambient temperature (e.g., 25° C.) or other temperatures (e.g., 35° C., 37° C. or 40° C.).

In some embodiments, the target matrix is a target tissue. The delivery method may comprise introducing a bioconjugate to a target tissue under a physiological condition, for example, a physiological temperature of 35-39° C. In one particular embodiment, the bioconjugate is introduced to a target matrix at 37° C. and then the temperature is increased to at least 43° C.

After the bioconjugate is introduced to the target matrix, the temperature of the target matrix may be increased by at least 1, 2, 3, 4, 5, 10, 20, 40 or 50° C. or increased to at least 43° C. or 80° C.

The delivery method may further comprise exposing the target matrix to a trigger after introducing the bioconjugate to the target matrix. Such exposure may stimulate or improve disassembly of the particles of the bioconjugate introduced to the target matrix. The trigger may be a decrease in temperature, pH changes, metal ion binding, light exposure, changes in thiol concentration, changes in glutathione concentration or the presence of enzymes. The light exposure may include irradiation with UV, visible, or near-IR light.

The delivery method may further comprise decreasing the temperature of the target matrix to, for example, less than about 30° C., 25° C. or 4° C., after introducing the bioconjugate to the target matrix. In some embodiments, the target matrix is a target tissue, and the temperature of the target tissue is decreased by applying ice to the target tissue.

The delivery method may further comprise a pH change at the target matrix after introducing the bioconjugate to the target matrix. In some embodiments, the target matrix is a target tissue having a pH of 6.5-7.5 (e.g., pH of 7.0) when the bioconjugate is introduced in the form of particles to the target tissue, and the pH of the target tissue may be subsequently changed to be acidic (e.g., a pH of less than about 6.5) or basic (e.g., a pH greater than about 7.5).

The delivery method may further comprise exposing the target matrix to a metal ion such as a divalent metal ion after introducing the bioconjugate to the target matrix. As a result, the bioconjugate may be exposed to the metal ion after being introduced to the target matrix.

The delivery method may further comprise exposing the target matrix to light such as UV, visible or near-IR irradiation. As a result, the bioconjugate may be exposed to the light such as UV, visible or near-IR irradiation after being introduced to the target matrix.

The delivery method may further comprise changing thiol concentration of the target matrix after introducing the bioconjugate to the target matrix. For example, the thiol concentration of the target matrix is changed to about 100 µM, 1 µM, 5 µM or 10 µM.

The delivery method may further comprise changing glutathione concentration of the target matrix after introducing the bioconjugated to the target matrix. For example, the glutathione concentration of the target matrix is changed to about 100 µM, 1 µM, 5 µM or 10 µM.

Where the target matrix is a target tissue, the delivery method may further comprise binding the bioconjugate specifically to the target tissue. The target tissue may be a natural tissue in an organism or isolated from an organism. The target tissue may be an artificial tissue. The target tissue may be a combination of natural and artificial tissues. The target tissue may comprise collagen. Exemplary target tissues include articular cartilage, osteoarthritic cartilage, rheumatoid arthritis tissues, tumors, skeleton, heart tissues and blood vessels.

In the delivery method according to the present invention, the particles may carry a cargo molecule when the bioconjugate is introduced in the form of particles to the target matrix, and the cargo molecule may be released to the target matrix upon disassembly of the particles. The cargo molecule may be encapsulated in the particles, for example, in an aqueous lumen of the particles, or embedded within the particles, for example, in the hydrophobic interior part of a bilayer of the particles. The cargo molecule may be immobilized to the particles, for example, attached to the particle chemically or physically.

The target matrix may have a disease or condition, and the cargo molecule may be a therapeutic agent for treating the disease or condition. The released cargo molecule may be in an amount effective for treating the disease or condition. Where the target matrix is a target tissue, the disease or condition may be osteoarthritis, rheumatoid arthritis or cancer.

Example 1. Noncovalent Modulation of the Inverse Temperature Transition and Self-Assembly of Elastin-b-Collagen-Like Peptide Bioconjugates Stimuli-responsive nanostructures produced with peptide domains from the extracellular matrix offer great opportunities for imaging and drug delivery. Although the individual utility of elastin-like (poly)peptides and collagen-like peptides in such applications has been demonstrated, the synergistic advantages of combining these motifs in short peptide conjugates has surprisingly not been reported. Here, we introduce the conjugation of a thermoresponsive elastin-like peptide (ELP) with a triple-helix-forming collagen-like peptide (CLP) to yield ELP-CLP conjugates that show a remarkable reduction in the inverse transition temperature of the ELP domain upon formation of the CLP triple helix. The lower transition temperature of the conjugate enables the facile formation of well-defined vesicles at physiological temperature and the unexpected resolubilization of the vesicles at elevated temperatures upon unfolding of the CLP domain. Given the demonstrated ability of CLPs to modify collagens, our results provide not only a simple and versatile avenue for controlling the inverse transition behavior of elastin-like peptides, but also suggest future opportunities for these thermoresponsive nanostructures in biologically relevant environments.

We postulated that the conjugation of short ELPs with CLP domains would offer significant opportunities in the design and application of thermoresponsive nanoparticles, and report here the facile chemical production of these conjugates and their unexpected thermally responsive behavior. The CLP sequence (GPO)$_4$GFOGER(GPO)$_4$GG (SEQ ID NO: 8) was employed, owing to the fact that CLPs with 8 or more GPO repeats exhibit melting temperatures ($T_m$) above 37° C., which enables formation of stable triple helix at physiological temperature. The peptide sequence GFOGER (SEQ ID NO: 5) was employed owing to the fact that it is widely recognized by several kinds of integrins such as $\alpha_1\beta_2$, $\alpha_2\beta_1$, and $\alpha_{11}\beta_{11}$. It has been reported more recently that the introduction of the GFOGER (SEQ ID NO: 5) peptide in a PEG-based hydrogel not only provides a better chondrogenic microenvironment compared with that imparted by the RGD peptide, but also enhanced gene expression of type II collagen. Based on these investigations, inclusion of the GFOGER (SEQ ID NO: 5) domain should facilitate the binding of these materials with cells in future studies. An ELP with the sequence (VPGFG)$_6$ (SEQ ID NO: 21) was introduced as the thermoresponsive domain, as it would be expected to have a $T_t$ below 37° C., allowing the conjugate to assemble via collapse of the ELP domain at physiological temperature.

An alkyne-functionalized ELP and azide-functionalized CLP were synthesized via standard Fmoc-based solid-phase peptide synthesis methods and purified via reverse-phase high-performance liquid chromatography (HPLC). The purity and expected composition of the peptides was verified by analytical HPLC and ESI-MS, respectively. The ELP was then conjugated to the CLP in DMF via standard CuAAC methods (FIG. 1); successful synthesis and purification of the conjugates in high yield were verified via gel permeation chromatography, $^1$H NMR spectroscopy, as well as FT-IR spectroscopy.

The ability of the CLP domain to form stable triple helix at physiological temperature while conjugated to the ELP was probed via circular dichroic spectroscopy (CD). The CD spectra of ELP-CLP at temperatures ranging from 5° C. to 80° C. (FIG. 2a) show a clear maximum at ca. 225 nm, indicating that the CLP domain is competent to form triple helical structures after conjugation with ELP. The reduction of the intensity of the peak with increasing temperature (FIG. 2b) indicates the expected unfolding of the triple helix upon heating, with the first derivative of the melting curve (after correction for the contribution from the ELP) suggesting a $T_m$ of ca. 57° C. for the CLP-ELP conjugate, which is significantly higher than that of the isolated CLP (ca. 50° C.). Presumably, the collapse of the ELP domain at the elevated temperatures anchors the CLP and stabilizes it against unfolding, similar to our previously reported results for a polymer-conjugated CLP. The refolding of the CLP triple helix (FIGS. 2c and 2d) is likewise accelerated by the ELP anchoring of the CLP, owing to the increase in the local concentration of the CLP strands. While a rate constant of $1.14 \times 10^7$ $M^{-2} \cdot s^{-1}$ was observed for the refolding reaction of the CLP, the diblock shows a higher rate constant of $4.63 \times 10^7$ $M^{-2} \cdot s^{-1}$.

Figure 3:
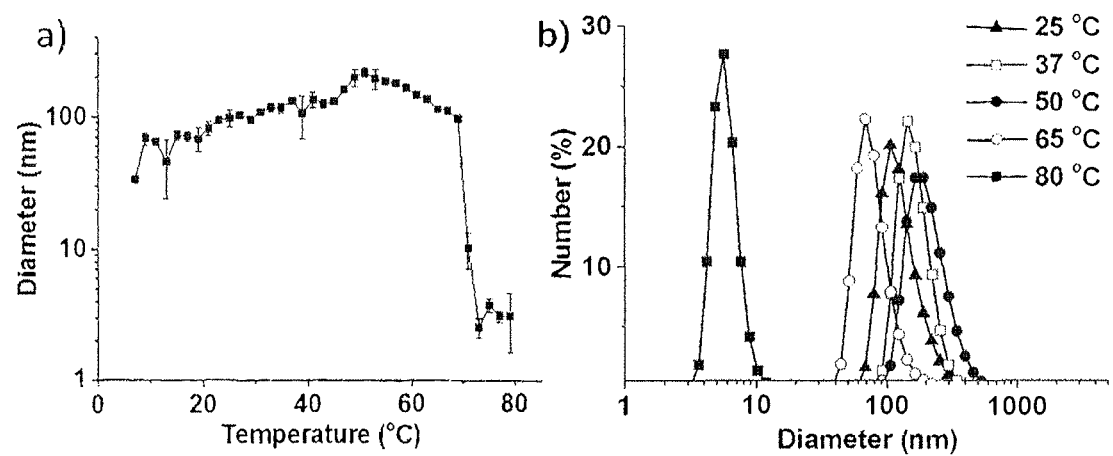
FIG. 3 shows dynamic light scattering characterization of the assembly of ELP-CLP conjugates. a) Hydrodynamic diameter of nanostructures as a function of temperature upon heating; b) Size distributions of ELP-CLP assemblies at select temperatures.
Figure 4:
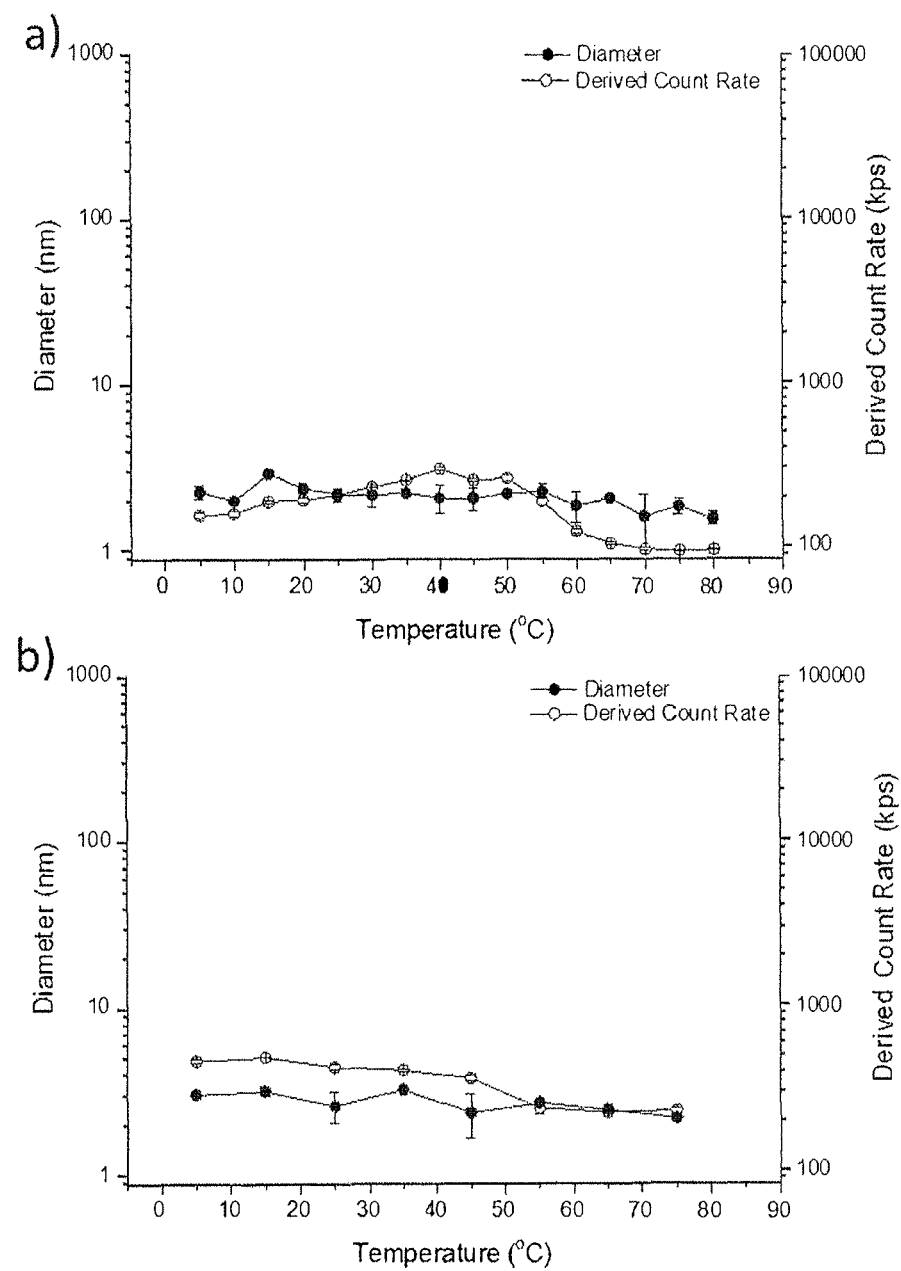
FIG. 4 shows the measured hydrodynamic diameters of CLP/ELP assemblies as a function of temperature upon heating. (A) ELP at 1 mg/mL in water; (B) ELP and CLP physical mixture at 0.5 mg/mL each in water.

The anticipated assembly of ELP-CLP nanostructures at physiologically relevant temperatures was confirmed via dynamic light scattering (DLS) (FIG. 3). In contrast to our expectations that nanoparticle formation would be triggered at near physiological temperature, however, the conjugates formed structures with hydrodynamic diameters ($D_h$) that ranged from approximately 50 to 200 nm at all temperatures between 4° C. and 65° C. (FIG. 3a), with a $D_h$ of approximately 160 nm at 37° C. (FIG. 3b). These results are counterintuitive based on the expected increase of the transition temperature of thermoresponsive polymers and ELPs with conjugation to a hydrophilic domain and the observation that the ELP alone does not undergo a transition at Tt. Instead, conjugation of the short ELP to a hydrophilic CLP results in a dramatic reduction of the $T_t$ of the ELP to below 4° C.; the lack of aggregation of the ELP alone (FIG. 4) indicates that this reduction exceeds 80° C.

Just as the CLP triple helix is stabilized at high temperature by the anchoring effect of ELP coacervation, the unexpected assembly of the ELP-CLP conjugates at low temperatures is almost certainly attributable to the anchoring effects of the CLP triple helix, which would serve to locally isolate three ELP domains at concentrations approximately 100-fold higher than that of the ELP monomers in solution.

Figure 2:
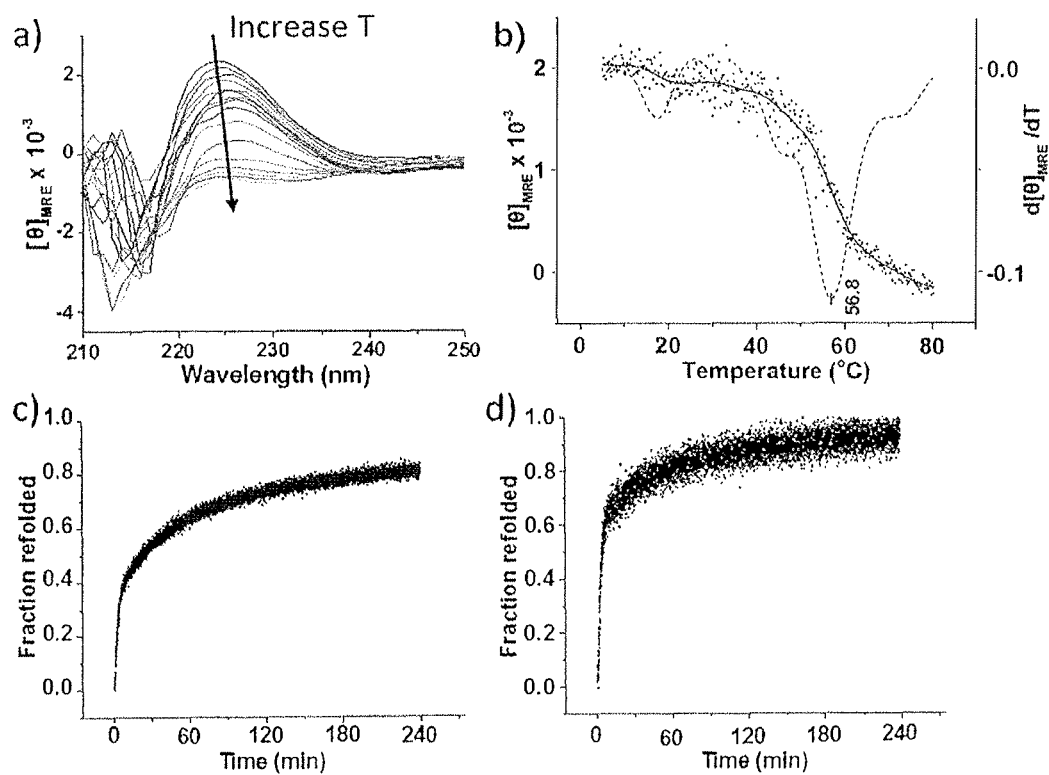
FIG. 2 shows a) CD spectra showing representative full-wavelength scans for the ELP-CLP conjugate; b) Thermal unfolding profile for an ELP-CLP conjugate; the first derivative of the unfolding curve with respect to temperature is shown in red; c) Refolding profile of CLP after quenching from 80° C. to 5° C.; d) Refolding profile of the ELP-CLP conjugate after quenching.

The anchoring of the ELP by the noncovalent formation of CLP triple helix, however, should offer unique and as yet unreported opportunities to reversibly modulate the transition temperatures of the ELP domain and to thus confer dual thermoresponsiveness to the conjugates. Indeed, after an initial increase in the $D_h$ of the ELP-CLP nanoparticles with heating to 50° C. (FIG. 3), $D_h$ begins to decrease once the sample is heated above this temperature, which is also approximately the melting temperature of the CLP (FIG. 2b). With additional heating to 80° C., the CLP unfolds completely (FIG. 2b), and the nanoparticles become fully solubilized as monomers with an average $D_h$ of only 5.6 nm (FIG. 3b). Once the triple helix is unfolded and the ELP is no longer anchored, the $T_t$ of the unfolded ELP-CLP conjugate is above 80° C. (FIG. 5), which is consistent with our control results and with the expected behavior of the ELP with the addition of a hydrophilic CLP domain. This behavior is fully reversible, thus offering a new avenue for controlling the temperature responsiveness of short ELPs.

Figure 6:
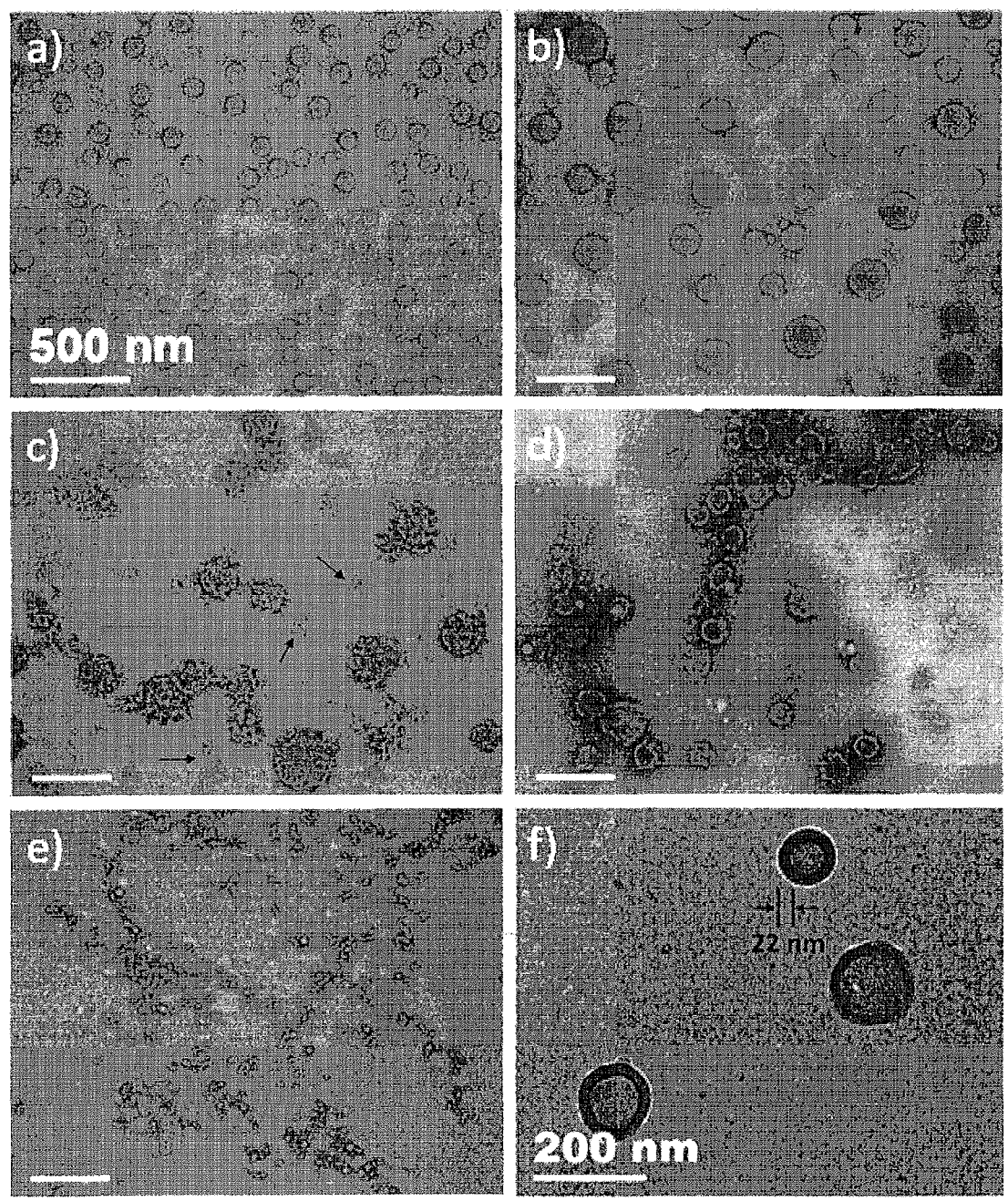
FIG. 6 shows a)-e) TEM images of nanoparticles from ELP-CLP conjugates at various temperatures, after negative staining with phosphotungstic acid. Scale bars: 500 nm. a) 25° C.; b) 37° C.; c) 50° C.; d) 65° C.; e) 80° C. f) Cryo-TEM image of nanoparticles of the ELP-CLP diblock at 25° C. Scale bar: 200 nm.

Transmission electron microscopy (TEM) was conducted to investigate the morphology of the nanostructures formed at 25° C., 37° C., 50° C., 65° C. and 80° C. (FIG. 6a-6e, respectively). Consistent with the DLS results, nanoparticles with an average diameter of approximately 80-100 nm were observed at room temperature, and the diameter of these particles increased to 150-250 nm at physiological temperature. Once the sample was heated above the $T_m$ of the collagen domain (50° C.), the nanoparticles showed some changes in morphology and size, with both porosity and apparent monomer (indicated by black arrows) observed at 50° C. (FIG. 6c), with increasing porosity and decreasing size when the temperature was raised to 65° C. (FIG. 6d). A vesicular structure is suggested for the nanoparticles, although only at the elevated temperatures, perhaps because the PTA stain was capable of diffusing into the porous nanoparticles and thus accumulating at both the exterior and interior surfaces of the vesicles. At 80° C. (FIG. 6e), the molecules are soluble and no defined nanostructure was observed.

Figure 5:
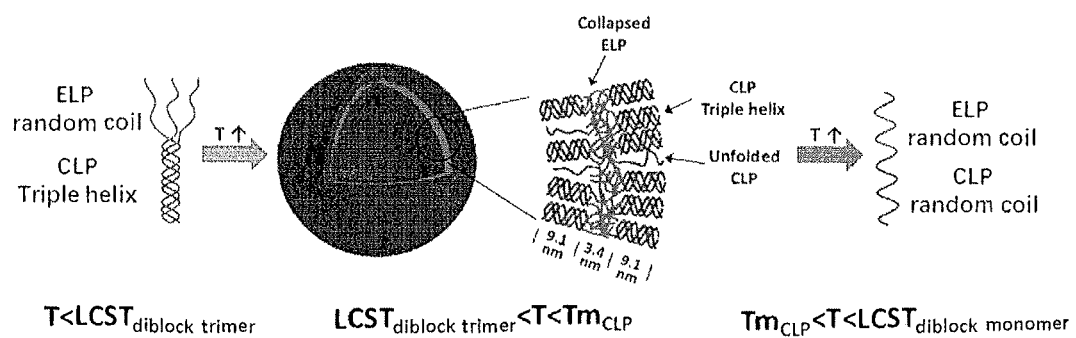
FIG. 5 illustrates Scheme 2, proposed assembly/disassembly and bilayer structure of ELP-CLP vesicles.

The vesicular structure of the nanoparticles was further confirmed via cryo-TEM of conjugates incubated at room temperature (FIG. 6f); vesicles with a diameter of approximately 100 nm were observed. Image analysis indicates that the thickness of the vesicle walls is 22±2 nm, which is consistent with the presence of two CLP triple helices (9.1 nm each) summed with the approximate $R_g$ of the collapsed ELP domains (3.4 nm). The results suggest a bilayer structure of the vesicle walls, with collapsed ELP domains in the center and CLP triple helical domains at both interior and exterior surfaces (FIG. 5). The presence of a small percentage of unfolded CLP chains is rendered in the schematic, to reflect the unfolding of the CLP domain observed in CD experiments.

The thermally induced assembly of ELP block copolypeptides has been a subject of intense investigation over decades. Essentially all previous reports, however, employ ELP-based recombinant polypeptides that mainly form micellar structures, although there are some reports of larger structures and nanostructures that exhibit additional sensitivity to pH and di-cations. There have been essentially no reports of thermoresponsive nanostructures that can be assembled from short synthetic ELPs. Our studies illustrate that this barrier can be overcome by simply anchoring three ELP chains to a collagen triple helix. This not only exploits the reversibility of triple helix formation to modulate the transition temperature of the molecules over a wide range, but should also permit manipulation of the size of the vesicles. In addition, there are few reports of the assembly of thermoresponsive collagen-like peptide containing copolymers, and none to our knowledge in which nanovesicles are produced. The likely location of the collagen domain at the exterior surface of the vesicles may serve as a means to localize nanoparticles in collagen-containing tissues, hydrogels, and films.

Figure 7:
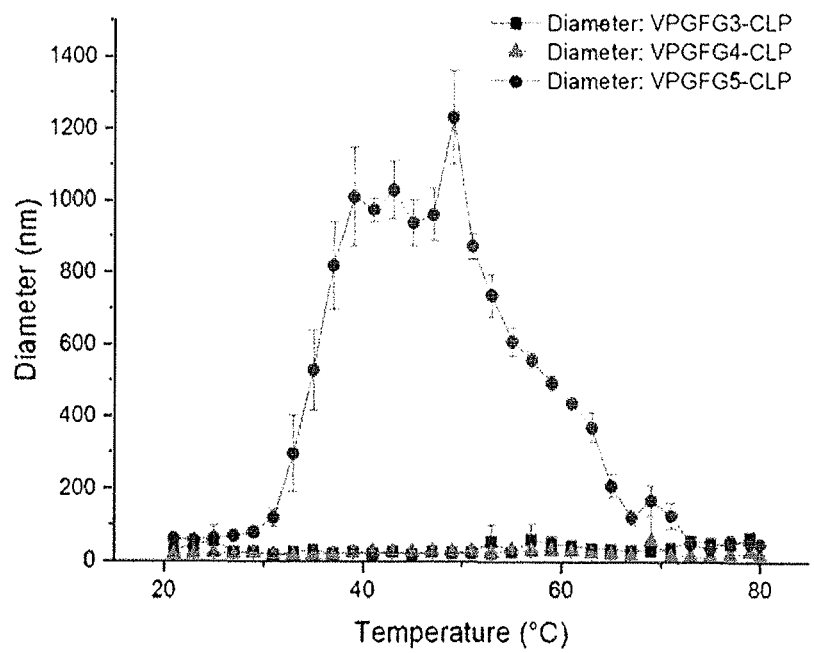
FIG. 7 shows the hydrodynamic diameters of (VPGFG)$_{3-5}$ (SEQ ID NOs: 18, 19 and 20)-CLP diblock assemblies as a function of temperature upon heating.

Simple variations in the relative lengths of the ELP and CLP domains, as well as variations in the sequences of the domains, offer a wide range of options for tailoring the thermoresponsive behavior of these systems. For example, preliminary studies of ELP-CLP conjugates with shorter ELP sequences ((VPGFG)$_{3-5}$) (SEQ ID NOs: 18, 19 and 20)) suggest that the transition temperature of nanoparticle formation and disassembly can be tuned to fall within the physiological range for the (VPGFG)$_5$ (SEQ ID NO: 20)-CLP (FIG. 7). The large size and polydispersity of the aggregates, however, suggests that the hydrophobic interactions of the shorter (VPGFG)s (SEQ ID NO: 20) are insufficient to form well defined nanoparticles. Changes to the stability of the CLP block, when balanced with the hydrophobicity of the ELP domain, could also be employed to impart triggered assembly/disassembly under select conditions. The prospects are promising for these approaches in drug delivery, imaging, and materials modification.

Example 2. Cargo Release from Nanoparticles in Solution

Figure 8:
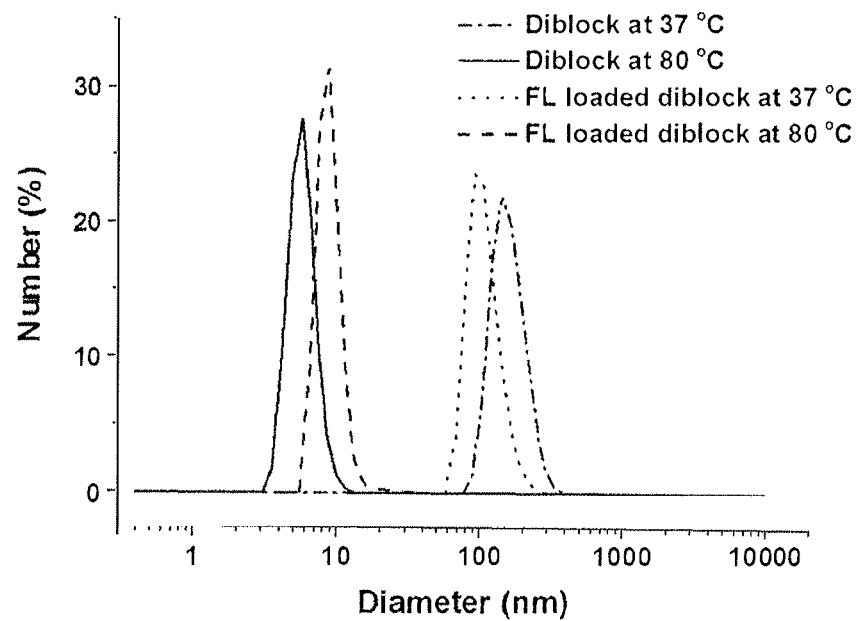
FIG. 8 shows the size distribution of ELP-CLP nanoparticles before and after fluorescein (FL) encapsulation at 37° C. and 80° C.
Figure 9:
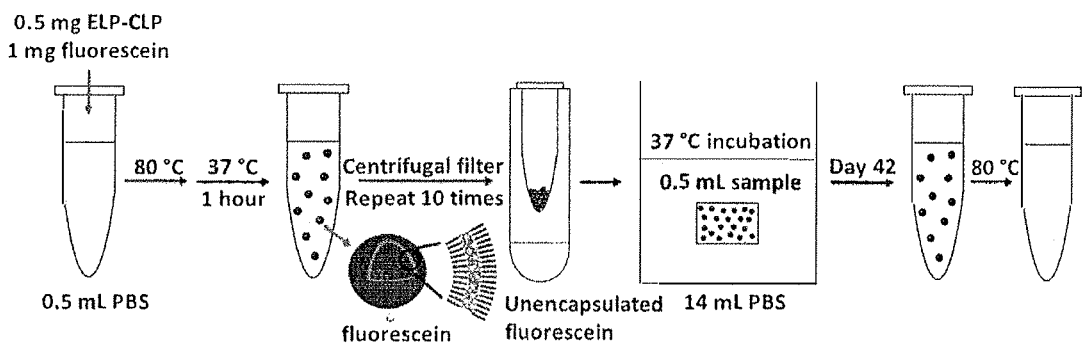
FIG. 9 shows release of fluorescein. (A) An example protocol for fluorescein encapsulation and release; and (B) The release profile of encapsulated fluorescein over a time period of 42 days. A burst release was observed at day 42, when the sample was heated at 80° C.
Figure 9:
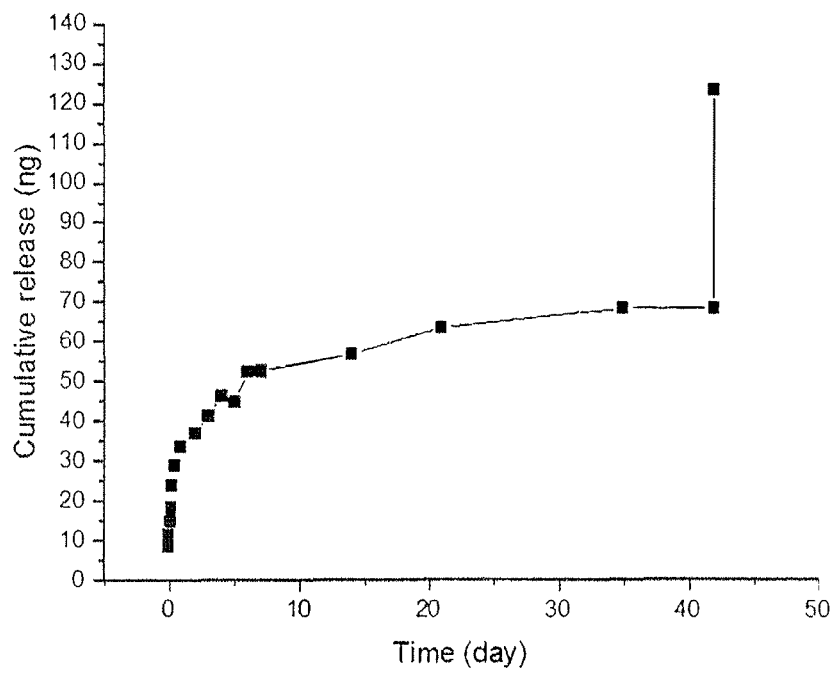

Fluorescein (FL, 2 mg in 50 μL DMSO) was added to a 1 mg/mL CLP-ELP aqueous solution at 4° C., followed by heating of the solution to 37° C. to allow nanoparticle formation and cargo encapsulation. The FL-loaded nanoparticles showed similar diameters as CLP-ELP nanoparticles without FL, at both 37° C. and 80° C. (FIG. 8). Unencapsulated cargo was removed via dialysis against water, and the sample incubated in PBS at 37° C. for over one month (FIG. 9A). Cargo concentrations at various timepoints over one week were determined by measuring fluorescence intensity at ca. 520 nm (after excitation at ca. 494 nm), and cumulative cargo release was calculated using standard protocols. Burst release of cargo was observed upon heating the sample to 80° C., which is above the triple helix transition of the CLP (FIG. 9B). Light scattering measurements (DLS) confirmed that release occurs with nanoparticle dissolution.

Example 3. Retention and Release of Bioconjugate Cargo from Collagen Films

Figure 10:
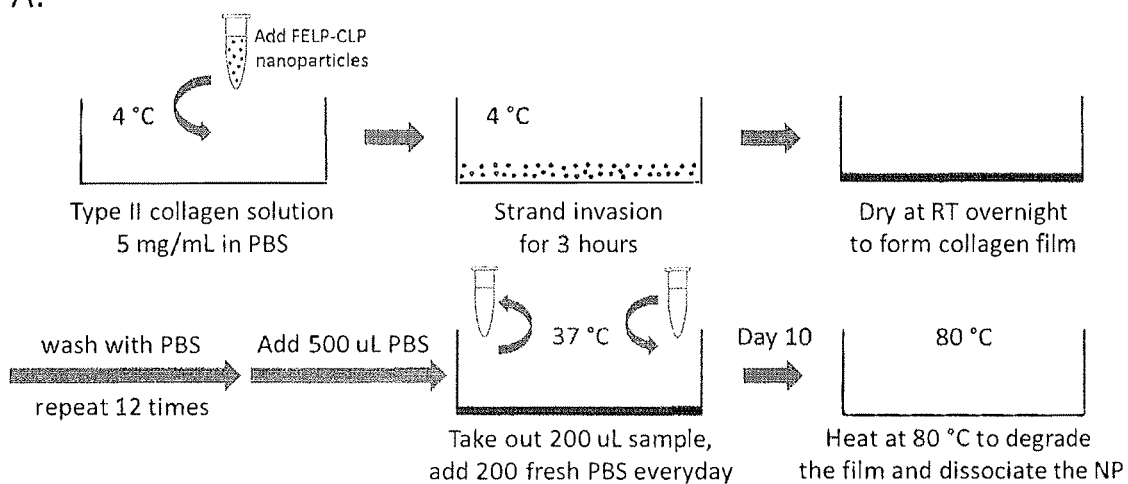
FIG. 10 shows collagen retention. (A) Example methods showing the preparation of type II collagen films modified with FELP-CLP nanoparticles and subsequent nanoparticle release over 10 days; and (B) The release profile of encapsulated FELP-CLP nanoparticles over 10 days. A burst release was observed at day 10, when the samples were heated at 80° C. Solid spheres: preheated FELP-CLP nanoparticle sample, which were preheated during preparation of the nanoparticle-modified films. Hollow spheres: non-preheated FELP-CLP nanoparticle control.
Figure 10:
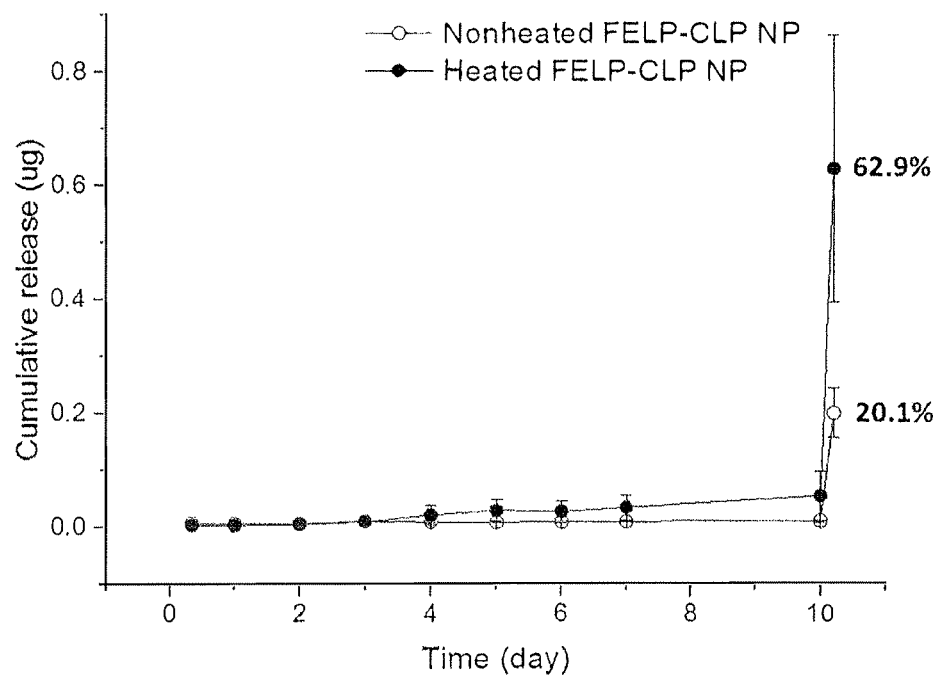

Type II collagen was dissolved at 5 mg/mL in 0.25% V acetic acid overnight. The pH of the collagen solution was then adjusted to 7-8 using 10×PBS and 1M NaOH. 30 μL ELP-CLP nanoparticle solution (210 μg/mL, preheated at 65° C.) was added into 600 μL collagen solution (4° C.). The cargo (initially fluorescein)-containing CLP-ELP nanoparticles (CLP-ELP-cargo at 1 mg/mL) were incubated briefly at ca. 50° C. to partially unfold the CLP triple helices; nanoparticles remain intact during this heating owing to the collapse of the ELP domain. A control sample was run in which this heating step at 50° C. was not conducted. The samples were then incubated at 4° C. for 3 hours to allow the nanoparticles to bind with the collagen membrane via strand invasion process. The collagen films were then gelled at 37° C. for 1 hour and dried overnight at room temperature. The collagen films were then washed with PBS until no fluorescence was detected in the wash to ensure all unembedded nanoparticles were removed. The full process is illustrated in FIG. 10A.

For the release of the nanoparticles from collagen films, 500 μL 1×PBS was added on the top of each film as a reservoir for the release. 200 μL sample was collected and 200 μL fresh PBS was added to each well at 8 h, 1 d, 2 d, 3 d, 4 d, 5 d, 6 d, 7 d. At day 10, 200 μL sample was collected, fresh PBS was not added. The samples were then incubated at 80° C. for 1 hour to completely dissolve the film and dissociate the nanoparticles. Solutions became clear after incubation. 200 μL solution was then immediately collected from each sample and measured. The collagen films that were preheated with the nanoparticles to enable improved integration of the FELP-CLP nanoparticles into the films showed a greater amount of fluorescence upon dissolution of the collagen film (FIG. 10B). The very low amount of release prior to the final heating step illustrates that the FELP-CLP nanoparticles were strongly retained in the collagen film. While this example teaches the encapsulation and release of a small molecule fluorophore, use of the CLP-ELP platform for delivering larger molecules (e.g., AF488-3k dextran) and peptide-based candidate drugs (e.g., MMP-13 inhibitors such as PG-530742) is also possible.

Example 4. Interactions of ELP-CLP Nanoparticles with Cells

The bioconjugate particles do not cause significant activation of macrophages. RAW264.7 murine macrophages were purchased from American Type Culture Collection (ATCC) and were cultured in DMEM (Sigma Aldrich) supplemented with 10% heat-inactivated fetal bovine serum (MediaTech), 10 mM HEPES (GIBCO), 55 μM β-mercaptoethanol (GIBCO), and 1% antibiotic/antimycotic (GIBCO) at 37° C. with 5% $CO_2$. Upon reaching 60-80% confluency, cells were lifted off the plates by gentle scraping and seeded on a 96-well plate at a density of 5×10$^4$ cells per well in 200 μL cell culture media. After an overnight incubation and media change, cells were treated with various concentrations of ELP-CLP nanoparticles (50, 150, 500, and 1000 µg/mL) in medium. Cells treated with lipopolysaccharide (LPS, 50 ng/mL) served as a positive control, while cells in culture medium were utilized as a negative control. After 8 h of incubation, the supernatant was collected and stored at −20° C. until further analysis. Cell metabolism post-treatment was assayed using PrestoBlue Viability Assay (Life Technologies), which provides a fluorescence measurement of the overall reductive capability of the cells, according to the manufacturer's instructions. Briefly, 20 µL of reagent was added to 100 µL of cells and medium. After 2 h of incubation at 37° C., the medium was collected and analyzed using a PerkinElmer VICTOR3 1420 Multilabel Plate Reader (PerkinElmer, Waltham, Mass.) at excitation/emission wavelengths of 570 nm/615 nm. TNF-α concentration in collected media samples was measured via an enzyme-linked immunosorbant assay (ELISA) (BD Bioscience), according to the manufacturer's instructions.

The RAW 264.7 macrophages exhibited essentially 100% viability at all concentrations of nanoparticle tested (FIG. 11A), indicating the cytocompatibility of the nanoparticles. In addition, at all concentrations of nanoparticles tested, essentially no TNF-α expression above that of a negative control was observed, illustrating the lack of an inflammatory response initiated by the nanoparticles (FIG. 11B). In contrast the positive LPS control elicited high levels of TNF-α expression, as expected (FIG. 11B).

Figure 12:
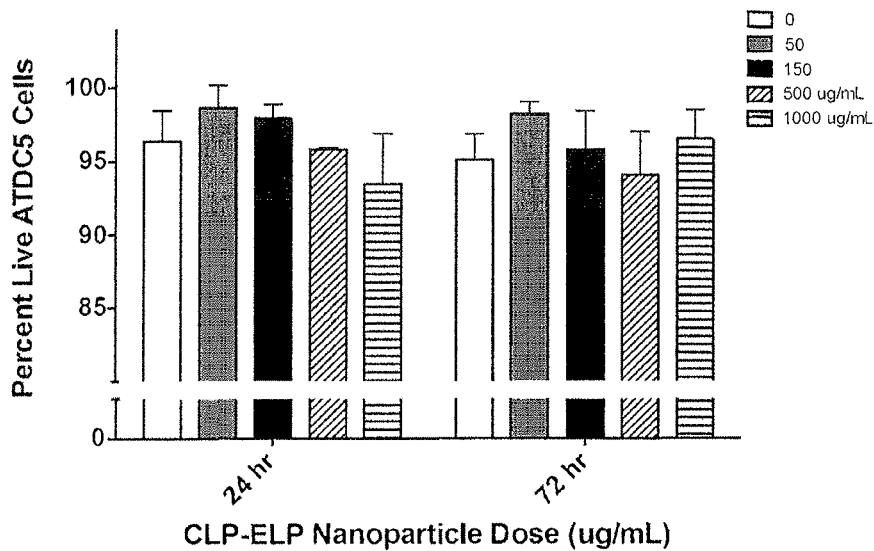
FIG. 12 shows the percentages of live ATDC5 cells treated with ELP-CLP nanoparticles at various concentrations for 24 h and 72 h.

The cytocompatibility of the ELP-CLP nanoparticles was also tested in the presence of ATDC5 chondrocytes under standard culture conditions (FIG. 12). Nanoparticles were added at 0 hr. NPs were tested at 0-, 50-, 150-, 500-, and 1000-ug/mL in the media. LIVE/DEAD assay was performed at 24- and 72-hours following NP addition in separate wells (not repeated measures). At each time-point the cells were imaged via fluorescence microscopy, in the same central position in each well, and the number of live (green) cells and dead (red) cells was quantified. Percent Live ATDC5 cells are defined as Live/(Live+Dead), and the number of wells measured at each conditions was 2-4. There were no significant differences in the viability of cells in the presence or absence of CLP-ELP nanoparticles at either time investigated. Viability ranged from 93.5 to 98.6% (FIG. 12).

Figure 13:
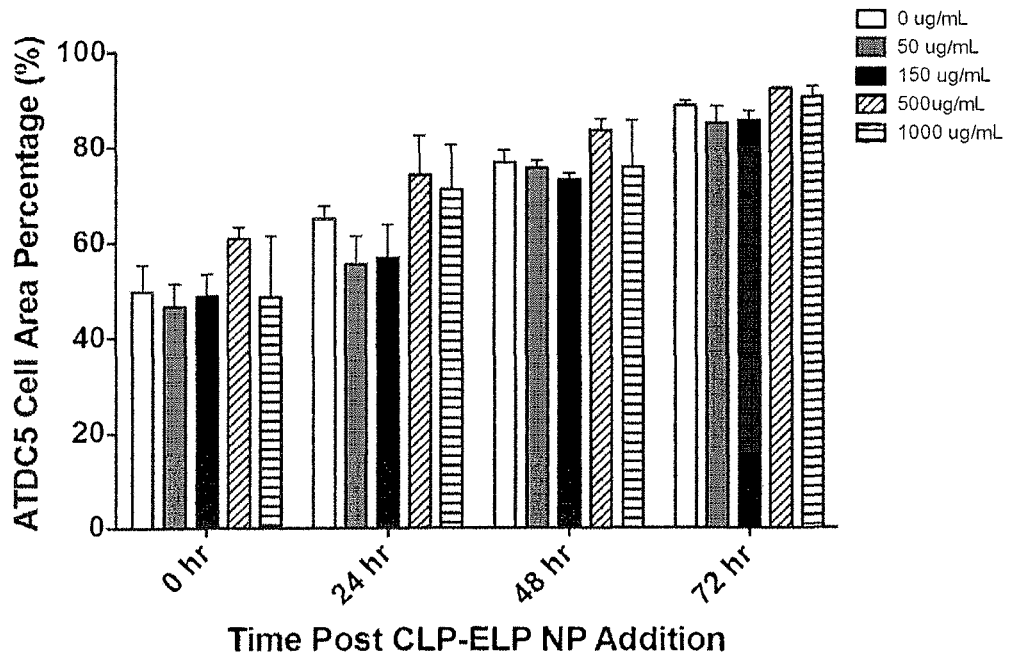
FIG. 13 shows ATDC5 cell proliferation after treatment with ELP-CLP nanoparticles, at various concentrations, for 0 h, 24 h, 48 h and 72 h.

The proliferation of ATDC5 cells was also measured (FIG. 13). As above, nanoparticles were added at 0 hr and were tested at 0-, 50-, 150-, 500-, and 1000-ug/mL concentration in media. At each time-point the cells were imaged on a bright field microscope, in the same central position in each well, and the fraction of the picture area that was covered by cells was quantified using a custom MATLAB code. This is indirectly indicative of cell proliferation/growth. The number of measurements (n) was 2-4 wells per experimental condition. There was no significant differences in the cell area percentage in the presence of CLP-ELP nanoparticles at any of the times investigated (FIG. 13).

Figure 14:
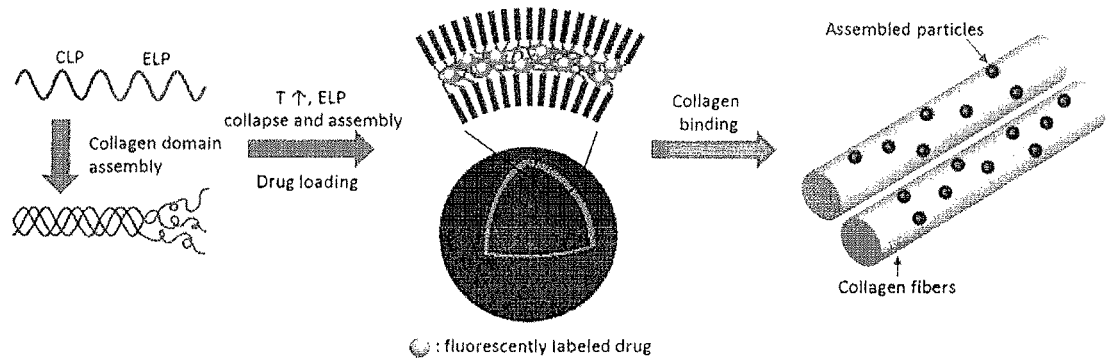
FIG. 14 illustrates a scheme showing drug encapsulated ELP-CLP nanoparticles targeting collagen fibers via strand invasion, followed by in situ drug release from the nanoparticles.
Figure 15:
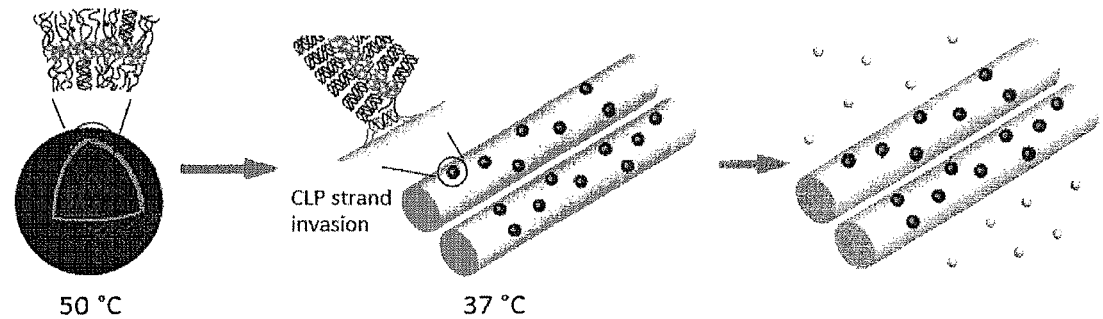
FIG. 15 illustrates proposed materials and approaches for generating collagen-binding, thermoresponsive, vesicle-like nanoparticles for drug delivery.
Figure 16:
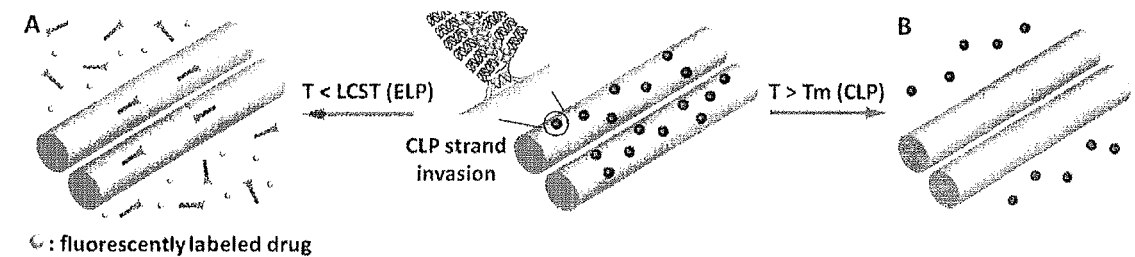
FIG. 16 shows temperature-triggered release from nanoparticles with dual temperature responsiveness. Disassembly of either (A) the ELP domains at decreased temperature or (B) the CLP-collagen interactions at increased temperature.

Example 5. Controlled Release from Bioconjugates Under Conditions Relevant for Treating Disease We describe an extremely simple strategy that exploits the specific binding of CLPs to develop novel, thermoresponsive conjugates that could be used to target collagen-containing tissues, including damaged cartilage tissues. The basis of these strategies is our pioneering observations that CLP-containing conjugates comprising elastin-like peptides (ELPs) can assemble into cargo-loaded, hollow nanoparticles of clinically relevant sizes (~100 nm) and can be thermally triggered to disassemble and release clinically relevant amounts of encapsulated cargo. We will also take advantage of our additional observation that collagen-peptide modified nanoparticles can be selectively retained in collagen matrices (in vitro and in vivo) for multiple weeks. Approaches coupling these methods will be uniquely suited for the encapsulation of drugs and their targeting to pathological collagen in an OA joint (FIG. 14), which will allow for passive extended release (FIG. 15) or for triggered release, if desired, upon hypothermic OR hyperthermic treatments (FIG. 16). This delivery strategy should be applicable to many drugs and easily implemented clinically.

Temperature-controlled binding of nanoparticles with collagen ex vivo to OA cartilage explants and triggering the release of encapsulated cargo can be achieved with CLP-ELP nanoparticles. While previous studies have illustrated the versatility of the ELPs as self-assembling amphiphiles, none have combined CLPs with ELPs to develop collagen-integrating, thermoresponsive nanostructures that can be employed clinically to both target delivery of drugs and thermally control drug release via simple elevation or reduction in temperature. The incorporation of an appropriate thermoresponsive ELP will enable modulation of drug release via simple reduction in temperatures (to ca. 25-30° C., easily obtained by treatment of the joint with ice), that would solubilize the CLP-ELP nanoparticles and trigger bulk release of the drug (FIG. 16A). In addition, the CLP domain of the CLP-ELP conjugates could also be engineered to unfold upon heating, thus providing an additional mechanism to release drug-loaded nanoparticles from collagen (FIG. 16B).

It is important to note that short synthetic ELPs have not been used in these types of investigations, almost certainly because of their normally high solubility in aqueous solution. By anchoring multiple ELPs with a collagen-like triple helix, however, we have successfully tuned the transition temperature to occur below physiological temperature, while endowing the nanostructure with the ability to bind to collagen. Based on the bilayer vesicular structure of the nanoparticles, the nanoparticles are capable of encapsulating hydrophilic drugs in the aqueous interior of the vesicle-like nanoparticles, as well as encapsulating hydrophobic drugs in the collapsed ELP domain. The CLP-ELP nanoparticles can show robust binding to collagen as well.

Figure 17:
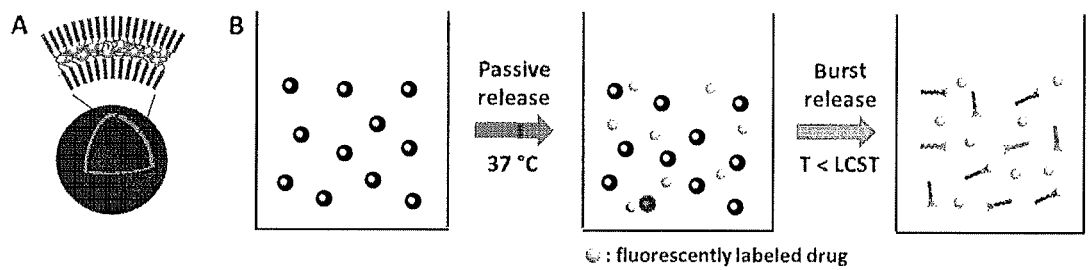
FIG. 17 illustrates the temperature-controlled release of encapsulated cargo from CLP-ELP nanoparticles in solution to monitor the role of nanoparticle assembly in encapsulation and release of a model drug. (A) Hydrophobic drug encapsulated in the collapsed ELP domain. (B) Long-term incubation at 37° C. and subsequent dissolution of the nanoparticles at 4° C.

The transition temperature for particle formation can be altered by tuning the transition temperature of the ELP domain by reducing its length and/or changing its composition; the transition temperature of ELP sequences (of the general identity (Val-Pro-Gly-Xaa-Gly)$_n$) (Val-Pro-Gly-Xaa-Gly; SEQ ID NO: 22) is highly dependent on the length of the peptide, as well as the hydrophobicity of the amino acid residue in the X position. Burst release of cargo is anticipated upon heating above the triple helix transition of the CLP, as we have demonstrated, and cargo will also be released upon cooling of the solution (FIG. 17B), to below the Tt of the bioconjugate, for example at 30° C. for the CLP-ELPs.

Human Cartilage Explants.

Articular cartilage from de-identified human OA tissue can be obtained as surgical waste following the performance of total knee arthroplasty. Plugs of healthy, and mild-to-moderate OA cartilage (ICRS grades 0 & 1-2, respectively), will be isolated and used for targeting of CLP-ELP nanoparticles to cartilage, as well as their retention and release of encapsulated cargo compounds. Similar to the collagen films, CLP-ELP nanoparticles containing labeled cargo (fluorescein, AF-dextran, labeled PG-530742) can be briefly heated at 50° C., followed by incubation with the OA cartilage plugs for three hours at 37° C. CLP-ELP targeting to damaged cartilage can be visualized and quantified via in situ confocal microscopy following a PBS wash (37° C.). The kinetics of passive release can be measured via fluorescence spectroscopy of encapsulated cargo. Burst release at 25-30° C. can also be measured.

In Vivo Application in a Murine Model of OA as an In Vivo Model for Human Applications.

Figure 11:
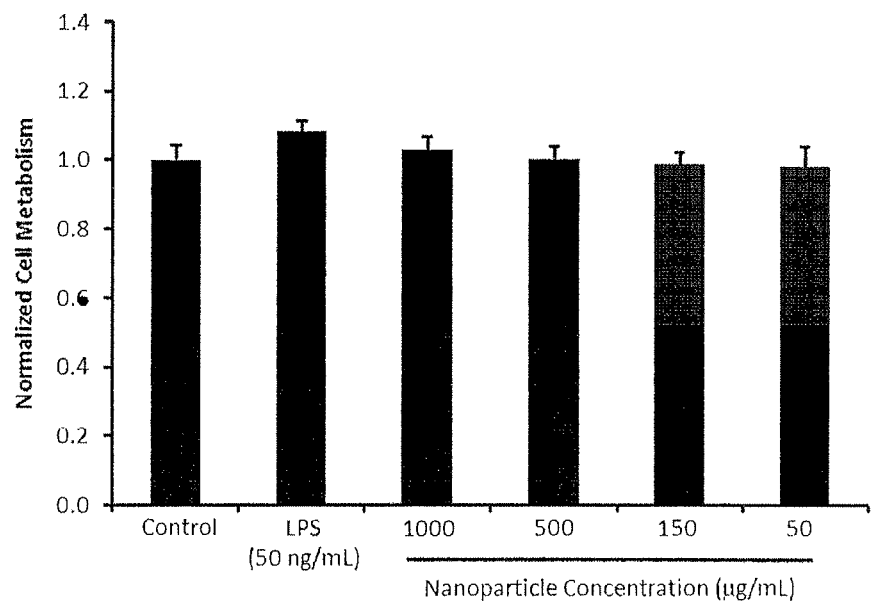
FIG. 11 shows an inflammation response study (RAW264.7 macrophage-like cell, TNFα production) (A) Normalized cell metabolism characterized via PrestoBlue viability assay for ELP-CLP nanoparticle solutions with various nanoparticle concentrations. Blank PBS was used as a negative control and lipopolysaccharide (LPS, 50 ng/mL) was used as a positive control; and (B) TNF-α production from RAW264.7 macrophages, treated with ELP-CLP nanoparticles at various concentrations. Blank PBS was used as a negative control and lipopolysaccharide (LPS, 50 ng/mL) was used as a positive control.
Figure 11:
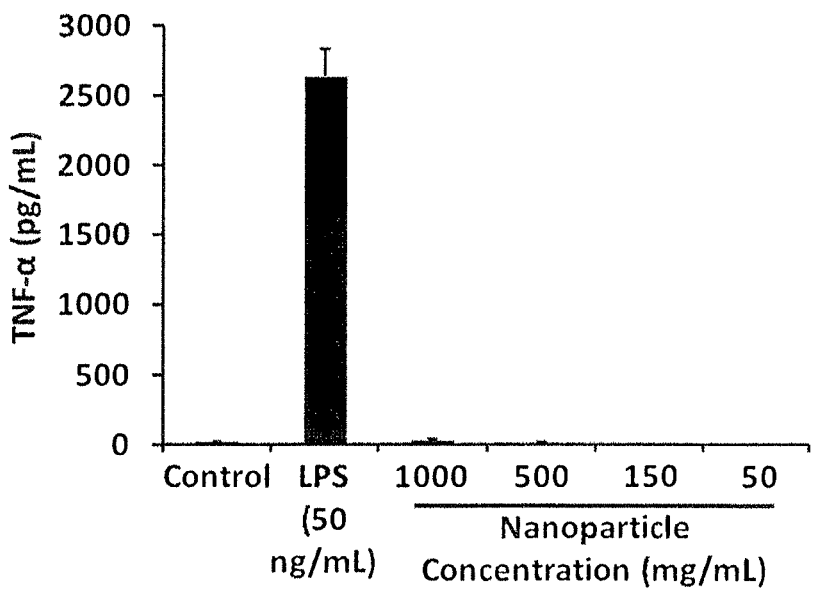
Figure 18:
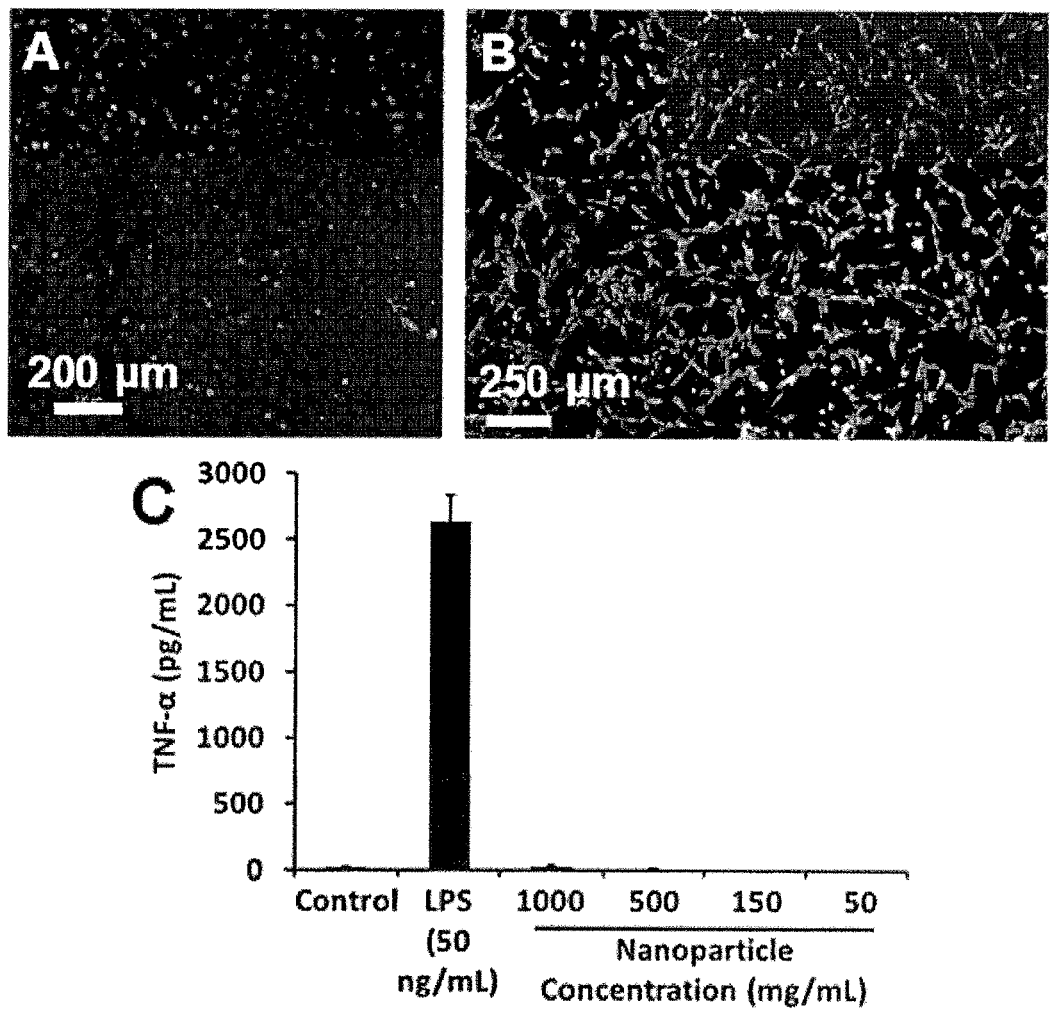
FIG. 18 shows (A) Cell viability data for chondrocyte (ATDC5) cultures (10,000 cells/cm$^2$ in DMEM/F12/5% FBS) in the presence of 150 μg/mL CLP-ELP nanoparticles; live/dead assay overlay results are shown. (B) Viability of NIH-3T3 fibroblasts (8,000 cells/cm$^2$ in DMEM/10% FBS); live/dead overlay shown. (C) TNF-α production from RAW264.7 murine macrophage-like cell culture (15,000 cells/cm$^2$ in DMEM/10% FBS) in the presence of various concentrations of CLP-ELP nanoparticles. No elevated TNF-α expression was observed for any samples; an LPS positive control showed elevated TNF-α expression.

Cargo-loaded CLP-ELP nanoparticles can be injected into the knees of 12-week old, male C57BL/6J mouse knee joints to demonstrate in vivo targeting, cargo-release, and biological safety of CLP-ELP nanoparticles. CLP-ELP nanoparticles covalently labeled with 4'-(aminomethyl) fluorescein and loaded with IRDye 800CW (a far-red fluorescent dye), can be administered via intra-articular (i.a.) injection (6 uL injection containing ca. 50-150 mg NP or free cargo equivalent in sterile saline) to naïve mouse knees (n=11 mice) or knees that have been subjected to DMM surgery two-weeks prior in order to induce a mid-degree of OA (n=11 mice). The IRDye 800CW will permit in vivo imaging of loaded CLP-ELP nanoparticles, while the fluorescein label permits imaging of CLP-ELP nanoparticles in tissue via confocal microscopy. Tissue targeting of cargo-loaded CLP-ELP nanoparticles and burst release due to local hypothermal (ice) therapy (n=3 mice each for naïve and DMM knees) and immune response due to four weekly repeated i.a. injections (n=5 mice), which mimic clinically-relevant dosing and treatment strategies, can also be assessed. We do not anticipate any significant immune response from CLP-ELP nanoparticles, based on ample literature precedent, and preliminary experiments demonstrating both (i) the excellent viability of chondrocytes and fibroblasts (FIG. 12, FIG. 13, and FIGS. 18A and 18B) and (ii) the complete lack of activation of macrophages exposed to high CLP-ELP concentrations (FIG. 11 and FIG. 18C).

TABLE 2

Sequences

| SEQ ID NO | Sequence |
|---|---|
| 1 | ASIARLEEKVKTLKAQNYELASTANMLREQVAQLGAP |
| 2 | ASTDTLQAETDQLEDEKYALQTEIANLLKEKEKLGAP |
| 3 | GDFNRQFLGQMTQLNQLLGEVKDLLRQQVKETSFLRNTIAECQACG |
| 4 | GEQTKALVTQLTLFNQILVELRDDIRDQVKEMSLIRNTIMECQVCG |
| 5 | GFOGER |
| 6 | GPOGPOGPOGEKGERGPOGPOGPO or (GPO)$_3$GEKGER(GPO)$_3$GG |
| 7 | GPOGPOGPOGPOGEKGERGPOGPOGPOGPO or (GPO)$_4$GEKGER(GPO)$_4$GG |
| 8 | GPOGPOGPOGPOGFOGERGPOGPOGPOGPOGG or (GPO)$_4$GFOGER(GPO)$_4$GG |
| 9 | GPOGPOGPOGPOGPOGEKGERGPOGPOGPOGPOGPO or (GPO)$_5$GEKGER(GPO)$_5$ |
| 10 | GPPGPPGPPGEKGERGPPGPPGPP |
| 11 | GPPGPPGPPGPPGEKGERGPPGPPGPPGPP |
| 12 | GPPGPPGPPGPPGPPGFOGERGPPGPPGPPGPPGPP |
| 13 | KLKELKSKLKELLKLELQAIKQYKELKAEKLEL |
| 14 | LKALEEKLKALEEKLKALEEK |
| 15 | RMKQIEDKLEEILSKLYHIENELARIKKLLGER |
| 16 | SDLGPQMLRELQETNAALQDVRDWLRQQVREITFLKNTVMECDACG |
| 17 | TQEDLLKKIMKLLKKQIKLLKKQIKMLKRLEKQ |
| 18 | VPGFGVPGFGVPGFG or (VPGFG)$_3$ |
| 19 | VPGFGVPGFGVPGFGVPGFG or (VPGFG)$_4$ |
| 20 | VPGFGVPGFGVPGFGVPGFGVPGFG or (VPGFG)$_5$ |
| 21 | VPGFGVPGFGVPGFGVPGFGVPGFGVPGFG or (VPGFG)$_6$ |
| 22 | VPGXG or Val-Pro-Gly-Xaa-Gly --> (VPGXG)$_n$ = (Val-Pro-Gly-Xaa-Gly)$_n$ |
| 23 | VPGXGVPGXGVPGXG or (VPGXG)$_3$ |
| 24 | VPGXGVPGXGVPGXGVPGXG or (VPGXG)$_4$ |
| 25 | VPGXGVPGXGVPGXGVPGXGVPGXG or (VPGXG)$_5$ |
| 26 | VPGXGVPGXGVPGXGVPGXGVPGXGVPGXG or (VPGXG)$_3$ |
| 27 | XPAVG |

TABLE 2-continued

Sequences

| SEQ ID NO | Sequence |
|---|---|
| 28 | XPGVG |
| 29 | GPOGPOGPOGFOGERGPOGPOGPO |
| 30 | GPOGPOGPOGPOGPOGFOGERGPOGPOGPOGPOGPO |
| 31 | GPPGPPGPPGPPGPPGFOGERGPPGPPGPPGPP |

O = hydroxyproline

The term "about" as used herein when referring to a measurable value such as an amount, a percentage, and the like, is meant to encompass variations of ±20% or ±10%, more preferably ±5%, even more preferably +1%, and still more preferably ±0.1% from the specified value, as such variations are appropriate.

All documents, books, manuals, papers, patents, published patent applications, guides, abstracts, and other references cited herein are incorporated by reference in their entirety. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed is:

1. A method for delivering a thermoresponsive bioconjugate to a target matrix, comprising
   (a) introducing a thermoresponsive bioconjugate self-assembled into particles to a target matrix, wherein the bioconjugate comprises a first molecule comprising an elastin-like peptide (ELP) having no more than 125 amino acids, a second molecule capable of forming an oligomer, and a linker connecting the first molecule with the second molecule, and wherein the ELP has 3-10 repeats of VPGXG (SEQ ID NO: 22), XPGVG (SEQ ID NO: 28) or XPAVG (SEQ ID NO: 27), wherein X is an amino acid, and
   (b) increasing or decreasing the temperature of the target matrix, whereby the particles are disassembled at the target matrix.

2. The method of claim 1, wherein the ELP is VPGXGVPGXGVPGXG (SEQ ID NO: 23), VPGXGVPGXGVPGXGVPGXG (SEQ ID NO: 24), VPGXGVPGXGVPGXGVPGXGVPGXG (SEQ ID NO: 25) or VPGXGVPGXGVPGXGVPGXGVPGXGVPGXG (SEQ ID NO: 26), wherein X is an amino acid.

3. The method of claim 1, wherein the ELP is VPGFGVPGFGVPGFGVPGFGVPGFGVPGFG (SEQ ID NO: 21).

4. The method of claim 1, wherein the second molecule comprises a peptide.

5. The method of claim 4, wherein the peptide is a collagen-like peptide (CLP).

6. The method of claim 5, wherein the CLP has 5-15 repeats of GPO or GPP, wherein O is hydroxyproline.

7. The method of claim 5, wherein the CLP is selected from the group consisting of GPOGPOGPOGFOGERGPOGPOGPO (SEQ ID NO: 29), GPOGPOGPOGPOGFOGERGPOGPOGPOGPO (SEQ ID NO: 8), GPOGPOGPOGPOGPOGFOGERGPOGPOGPOGPOGPO (SEQ ID NO: 30), GPPGPPGPPGPPGFOGERGPPGPPGPPGPP (SEQ ID NO: 31), GPPGPPGPPGPPGPPGFOGERGPPGPPGPPGPPGPP (SEQ ID NO: 12), GPOGPOGPOGEKGERGPOGPOGPOGPO (SEQ ID NO: 6), GPOGPOGPOGPOGEKGERGPOGPOGPOGPO (SEQ ID NO: 7), GPOGPOGPOGPOGPOGEKGERGPOGPOGPOGPOGPO (SEQ ID NO: 9), GPPGPPGPPGEKGERGPPGPPGPP (SEQ ID NO: 10) and GPPGPPGPPGPPGEKGERGPPGPPGPPGPP (SEQ ID NO: 11), wherein O is hydroxyproline.

8. The method of claim 5, wherein the CLP is GPOGPOGPOGFOGERGPOGPOGPO (SEQ ID NO: 8), wherein O is hydroxyproline.

9. The method of claim 4, wherein the peptide is a coiled-coil peptide (CCP).

10. The method of claim 9, wherein the CCP is selected from the group consisting of RMKQIEDKLEEILSKLYHIENELARIKKLLGER (SEQ ID NO: 15), LKALEEKLKALEEKLKALEEK (SEQ ID NO: 14), KLKELKSKLKELLKLELQAIKQYKELKAEKLEL (SEQ ID NO: 13), TQEDLLKKIMKLLKKQIKLLKKQIKMLKRLEKQ (SEQ ID NO: 17), SDLGPQMLRELQETNAALQDVRDWLRQQVREITFLKNTVMECDACG (SEQ ID NO: 16), GEQTKALVTQLTLFNQILVELRDDIRDQVKEMSLIRNTIMECQVCG (SEQ ID NO: 4), GDFNRQFLGQMTQLNQLLGEVKDLLRQQVKETSFLRNTIAECQACG (SEQ ID NO: 3), ASTDTLQAETDQLEDEKYALQTEIANLLKEKEKLGAP (SEQ ID NO: 2) and ASIARLEEKVKTLKAQNYELASTANMLREQVAQLGAP (SEQ ID NO: 1).

11. The method of claim 1, wherein the bioconjugate has formula (I):

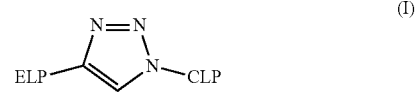

wherein the ELP is VPGFGVPGFGVPGFGVPGFGVPGFGVPGFG (SEQ ID NO: 21), and wherein the CLP is GPOGPOGPOGPOGFOGERGPOGPOGPOGPO (SEQ ID NO: 8), wherein O is hydroxyproline.

12. A thermoresponsive bioconjugate comprising a first molecule comprising an elastin-like peptide (ELP) having no more than 125 amino acids, a second molecule capable of forming an oligomer, and a linker connecting the first molecule with the second molecule, wherein the ELP has 3-10 repeats of VPGXG (SEQ ID NO:22), XPGVG (SEQ ID NO: 28) or XPAVG (SEQ ID NO: 27), wherein X is an amino acid, wherein the bioconjugate is self-assembled into particles, and wherein the particles are disassembled when the temperature is increased or decreased.

13. The bioconjugate of claim 12, wherein the ELP is VPGXGVPGXGVPGXG (SEQ ID NO: 23), VPGXGVPGXGVPGXGVPGXG (SEQ ID NO: 24), VPGXGVPGXGVPGXGVPGXGVPGXG (SEQ ID NO: 25) or VPGXGVPGXGVPGXGVPGXGVPGXGVPGXG (SEQ ID NO: 26), wherein X is an amino acid.

14. The bioconjugate of claim 12, wherein the ELP is VPGFGVPGFGVPGFGVPGFGVPGFGVPGFG (SEQ ID NO: 21).

15. The bioconjugate of claim 12, wherein the second molecule comprises a peptide.

16. The bioconjugate of claim 15, wherein the peptide is a collagen-like peptide (CLP).

17. The bioconjugate of claim 16, wherein the CLP has 5-15 repeats of GPO or GPP, wherein O is hydroxyproline.

18. The bioconjugate of claim 16, wherein the CLP is selected from the group consisting of GPOGPOGPOGFOGERGPOGPOGPO (SEQ ID NO: 29), GPOGPOGPOGPOGFOGERGPOGPOGPOGPO (SEQ ID NO: 8), GPOGPOGPOGPOGPOGFOGERGPOGPOGPOGPOGPO (SEQ ID NO: 30), GPPGPPGPPGPPGFOGERGPPGPPGPPGPP (SEQ ID NO: 31), GPPGPPGPPGPPGPPGFOGERGPPGPPGPPGPPGPP (SEQ ID NO: 12), GPOGPOGPOGEKGERGPOGPOGPOGPO (SEQ ID NO: 6), GPOGPOGPOGPOGEKGERGPOGPOGPOGPO (SEQ ID NO: 7), GPOGPOGPOGPOGPOGEKGERGPOGPOGPOGPOGPO (SEQ ID NO: 9), GPPGPPGPPGEKGERGPPGPPGPP (SEQ ID NO: 10) and GPPGPPGPPGPPGEKGERGPPGPPGPPGPP (SEQ ID NO: 11).

19. The method of claim 1, wherein the temperature of the target matrix is increased.

20. The method of claim 1, wherein the temperature of the target matrix is decreased.

* * * * *